US010398829B2

(12) United States Patent
Chassot et al.

(10) Patent No.: US 10,398,829 B2
(45) Date of Patent: Sep. 3, 2019

(54) BAG HOLDER FOR AN INJECTION SYSTEM

(71) Applicant: Bracco Injeneering SA, Lausanne (CH)

(72) Inventors: Pierre Yves Chassot, Thoiry (FR); Nicolas Pawelczyk, Geneva (CH); Francois Vulliet, Evian (FR)

(73) Assignee: Bracco Injeneering SA, Lausanne (CH)

( * ) Notice: Subject to any disclaimer, the term of this patent is extended or adjusted under 35 U.S.C. 154(b) by 0 days.

(21) Appl. No.: 16/067,421

(22) PCT Filed: Dec. 21, 2016

(86) PCT No.: PCT/EP2016/082111
§ 371 (c)(1),
(2) Date: Jun. 29, 2018

(87) PCT Pub. No.: WO2017/114714
PCT Pub. Date: Jul. 6, 2017

(65) Prior Publication Data
US 2019/0009017 A1    Jan. 10, 2019

(30) Foreign Application Priority Data
Dec. 30, 2015  (EP) ..................................... 15203120

(51) Int. Cl.
*A61M 5/00*        (2006.01)
*A61M 5/14*        (2006.01)
(Continued)

(52) U.S. Cl.
CPC .......... *A61M 5/007* (2013.01); *A61M 5/1408* (2013.01); *A61M 5/1417* (2013.01);
(Continued)

(58) Field of Classification Search
CPC .. A61M 5/007; A61M 5/1408; A61M 5/1417; A61M 5/1452; A61M 5/1414; A61M 5/16827
See application file for complete search history.

(56) References Cited

U.S. PATENT DOCUMENTS 7,240,882 B2    7/2007  Degentesh et al.
2004/0210192 A1* 10/2004  Degentesh ........ A61M 5/14546
                                                  604/151

(Continued)

FOREIGN PATENT DOCUMENTS

DE    102010000593 A1    9/2011
WO    2013078545 A1    6/2013

OTHER PUBLICATIONS

PCT Search Report and Written Opinion for PCT/EP2016/082111, dated Apr. 3, 2017.

*Primary Examiner* — Bhisma Mehta
*Assistant Examiner* — William R Frehe
(74) *Attorney, Agent, or Firm* — Vivicar Law, PLLC

(57) ABSTRACT

A solution for injecting one or more fluids into a patient is proposed. A corresponding injection system (200;700) comprises one or more supply stations (105a; 105b) each one for supplying one of the fluids to be injected, wherein at least one of the supply stations (105a; 105b) comprises a bottle holder (115a; 115b) for holding a bottle (110a; 110b) containing the fluid to be injected, the bottle holder (115a; 115b) comprising a first connector (415;1135), and a cover (120a; 120b) for covering the bottle (110a; 110b) when held on the bottle holder (115a; 115b), the cover (120a; 120b) comprising a second connector (420) for mating with the first connector (415;1135) to mount the cover (120a; 120b) on the bottle holder (115a; 115b); said at least one supply station (105a; 105b) further comprises a bag holder (205a; 205b) for holding a bag (605) containing the fluid to be (Continued)

injected, the bag holder (205a;205b) comprising a further second connector (425) for mating with the first connector (415;1135) to mount the bag holder (205a;205b) on the bottle holder (115a; 115b) and a further first connector (430) for mating with the second connector (420) to mount the cover (120a; 120b) on the bag holder (205a;205b).

16 Claims, 10 Drawing Sheets

(51) Int. Cl.
*A61M 5/162* (2006.01)
*A61M 5/145* (2006.01)

(52) U.S. Cl.
CPC .......... *A61M 5/1452* (2013.01); *A61M 5/162* (2013.01); *A61M 2205/3368* (2013.01); *A61M 2205/3653* (2013.01)

(56) References Cited

U.S. PATENT DOCUMENTS

| | | | |
|---|---|---|---|
| 2008/0058720 A1 | 3/2008 | Spohn et al. | |
| 2008/0275422 A1* | 11/2008 | Ross | A61M 5/1483 604/408 |
| 2010/0059498 A1 | 3/2010 | Hansen et al. | |
| 2013/0197361 A1 | 8/2013 | Kaiser et al. | |
| 2013/0331810 A1* | 12/2013 | Bazala | A61J 1/16 604/414 |
| 2014/0224829 A1* | 8/2014 | Capone | F04B 49/06 222/23 |
| 2015/0005734 A1* | 1/2015 | Inoue | A61J 1/14 604/500 |

\* cited by examiner

BAG HOLDER FOR AN INJECTION SYSTEM

CROSS-REFERENCE TO RELATED APPLICATIONS

This application is the national stage application of corresponding international application number PCT/EP2016/082111, filed Dec. 21, 2016, which claims priority to and the benefit of European application no. 15203120.9, filed Dec. 30, 2015 all of which are hereby incorporated by reference in their entirety.

TECHNICAL FIELD

The present disclosure relates to the field of medical equipment. More specifically, this disclosure relates to injection systems.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The injection of fluids into patients is commonplace in several medical procedures. For example, a contrast agent (or contrast medium) may be injected, possibly along with a saline solution, to enhance contrast of target (body) features (for example, human body's structures or organs) within the patients in scan examinations thereof. Particularly, in imaging applications (wherein a visual representation of the interior of the patients is created in a non-invasive way without turning to surgery techniques) the use of the contrast agent makes the target features more conspicuous. As a result, target features that would otherwise be less distinguishable from other nearby features (for example, surrounding tissues) are highlighted. This significantly facilitates the task of clinicians in diagnostic applications, and particularly the identification and/or characterization of lesions, the monitoring of their evolution or response to medical treatments. For example, a iodine-based contrast agent (such as comprising iopamidol) is commonly used in Computed Tomography (CT) applications (such as for angiography investigations).

The contrast agent is usually injected into a blood vessel of a patient by an (automated) injection system. The injection system pressurizes the contrast agent and injects it into the patient under predetermined injection conditions, for example, at a predetermined flow rate and volume. In this way, the contrast agent may be injected in a controlled, safe and efficient manner.

Typically, the contrast agent is provided in (rigid) bottles. Therefore, the injection system is provided with one or more supply stations, each one for supplying the contrast agent to be injected from a corresponding bottle. For this purpose, the supply station comprises a bottle holder that holds the bottle (turned up-side-down) in position and connects it to a delivery arrangement for delivering the contrast agent to the patient. Typically, the supply station also comprises a protective cover, which is mounted on the bottle holder so as to protect the bottle held thereon from external accidental shocks.

The bottle holder and the protective cover define a (closed) chamber, which may also provide for a thermal insulation of the bottle. This facilitates maintaining a target temperature of the contrast agent to be injected during the scan examination. Indeed, the contrast agent generally has a relatively high viscosity. The viscosity of the contrast agent may adversely affect its correct injection in the patient (for example, since occurring at a flow rate lower than it is desired). In any case, this requires the application of a relatively high pressure (with an increase in complexity, and then cost, of the injection system). Moreover, the injection of the contrast agent with high viscosity and at high pressure is quite uncomfortable for the patient. However, the viscosity of most contrast agents may be reduced by increasing their temperature. Therefore, the contrast agent is generally pre-warmed before being injected by using a dedicated equipment (for example, a warmer) separated from the injection system. For example, contrast agents pre-warmed to a target temperature close to the body temperature (such as 35-37° C.) may halve their viscosity. In this way, it is easier to inject the contrast agent efficiently (for example, at the desired flow rate) with lower pressure (and then lower complexity and cost of the injection system) and higher comfort for the patient. Moreover, in order to mitigate the cooling of the contrast agent due to the inevitable heat loss, some injection systems comprise a heating device that is controlled to warm the contrast agent to be injected, so as to maintain it at the target temperature (i.e., close to the body temperature) during the whole scan examination.

The contrast agent may also be provided in (soft) bags or pouches. The bags are more compact than the bottles, so as to allow reducing the costs for their shipment and storage. Moreover, the bags may be completely squeezed after use, thereby simplifying their disposal. However, the bags may not be used in the (traditional) injections systems that are designed for the bottles, since the bags require a completely different structure for holding them and for connecting them to the delivery arrangement.

Alternatively, US-A-2014/0224829 discloses a fluid handling arrangement that comprises a hanger supporting a saline fluid source container such as a saline bag and a pair of fluid container supports for supporting fluid containers. Moreover, U.S. Pat. No. 7,240,882 discloses a fill station comprising a holding assembly that supports a medical fluid container (comprised of a U-shaped bracket and an adjustable strap) and two hook members for hanging bags.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of mounting a bag holder on the bottle holder.

Particularly, an aspect provides an injection system wherein at least one supply station comprises a bottle holder, a cover to be mounted on the bottle holder and a bag holder to be mounted on the bottle holder with the cover that is successively mounted on the bag holder.

A further aspect provides a corresponding method for operating said injection system.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
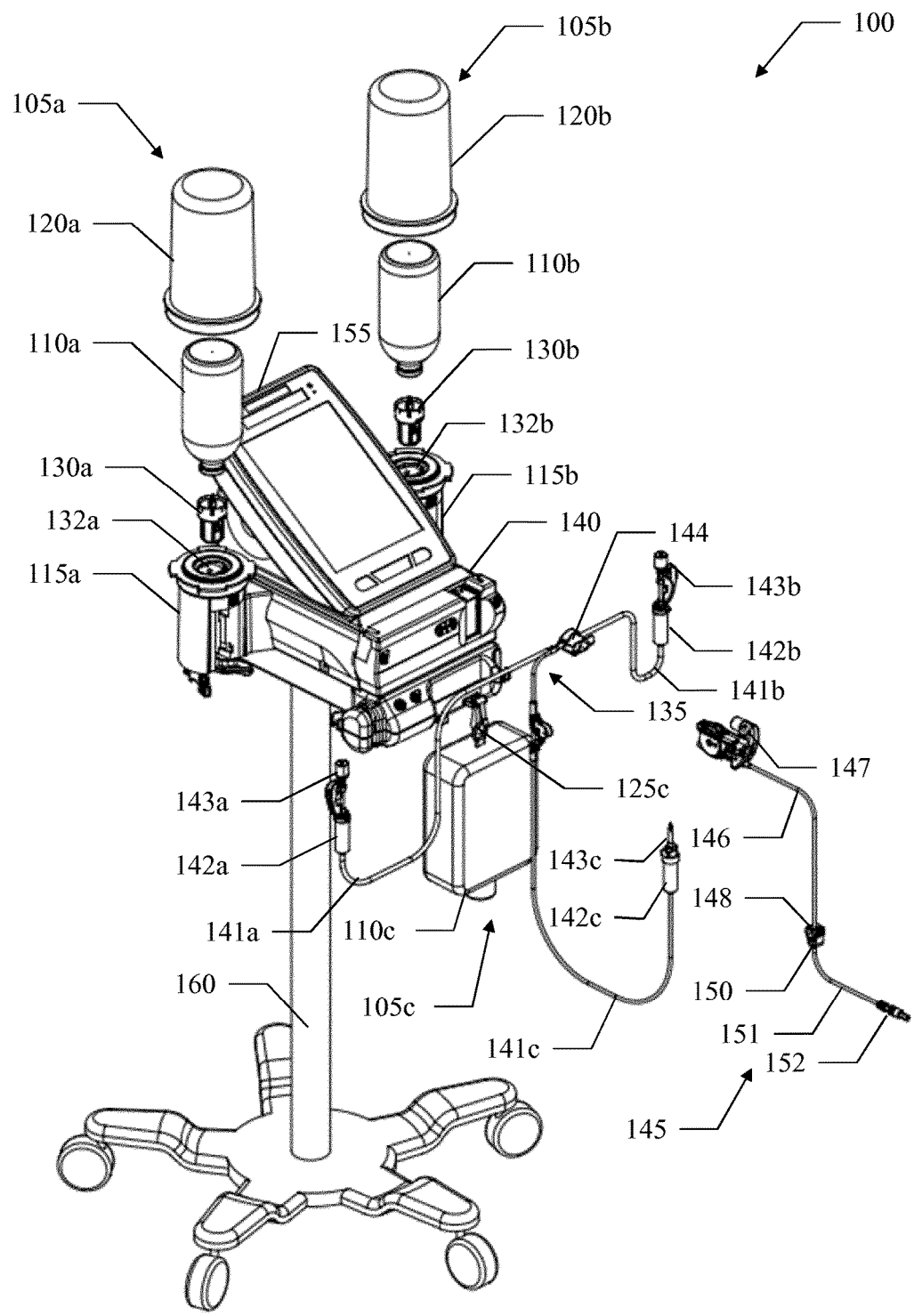
FIG. 1 shows a pictorial representation in partially exploded view of an injection system wherein the solution according to an embodiment of the present disclosure (not shown in the figure) may be applied.

With reference in particular to FIG. 1, a pictorial representation in partially exploded view is shown of an injection system 100 wherein the solution according to an embodiment of the present disclosure (not shown in the figure) may be applied.

The injection system 100 is used to inject one or more medical fluids into a patient (not shown in the figure). Particularly, the injection system 100 is an (automatic) contrast agent and saline solution (syringe-less) injector that is used by clinicians to perform scan examinations (for example, in radiography applications like CT applications).

The injection system 100 comprises a (left) supply station 105a, a (right) supply station 105b and a (front) supply station 105c for supplying the medical fluids to be injected from corresponding containers. Particularly, the supply station 105a and the supply station 105b supply a medical fluid from a bottle 110a and from a bottle 110b, respectively (i.e., a rigid container self-sustaining, for example, made of glass, and provided with a mouth at the end of a neck that is narrower than a main body thereof). The supply station 105c instead supplies a medical fluid from a pouch 110c (i.e., a soft container not self-sustaining, for example, made of plastic). The supply stations 105a,105b may be used to supply one or more contrast agents (to enhance contrast of specific body features within the patient) or a contrast agent and a saline solution (comprising a physiological or isotonic solution), whereas the supply station 105c may typically be used to supply the saline solution. For example, in CT applications the contrast agent may be a iodine-based contrast agent comprising diatrizoate, ioxaglate, iopamidol, iohexol, ioxilan, iopromide or iodixanol, and the saline solution may be sodium chloride. An example of a commercial contrast agent comprising iopamidol is ISOVUE manufactured by Bracco Diagnostics Inc. (trademarks). Each bottle 110a,110b may contain a single or multiple dose (for example, 50-500 ml) of different contrast agents (to be supplied in a predetermined sequence) or of the same contrast agent (to be supplied in succession to increase the duration of the scan examination). The pouch 110c generally contains a bulk of saline (for example, 100-1,000 ml) to be supplied before (pre-flush), after (post-flush) or between (interphase) injections of the contrast agent, or alternatively in rapid alternate succession with the contrast agent (to obtain a mixing of the contrast agent and the saline solution within an organ of the patient, for example, the heart). Alternatively, the supply stations 105a and 105b may be used to supply a contrast agent and a saline solution, respectively (without the use of the supply station 105c).

More specifically, each supply station 105a,105b (respectively) comprises a bottle holder 115a,115b for the bottle 110a,110b. A protective cover 120a,120b may be mounted on the bottle holder 115a,115b to cover the bottle 110a,110b when it is held thereon, thereby defining a (closed) chamber for housing the bottle 110a,110b. The bottle holder 115a, 115b and the protective cover 120a,120b protect the bottle 110a,110b from external accidental shocks. Moreover, they are made of a thermally insulating material (for example, polycarbonate) to reduce heat losses, thereby helping to maintain warm (for example, at about the body temperature) the medical fluid contained in the bottle 110a,110b. The supply station 105c instead simply comprises a hook 125c for hanging the pouch 110c.

A delivery arrangement creates a completely closed fluid pathway for delivering the medical fluids from the containers 110a,110b,110c to the patient.

For this purpose, in each supply station 105a,105b a bottle connector 130a,130b is arranged in a connection port 132a, 132b of the bottle holder 115a,115b. The bottle connector 130a,130b comprises a spike for connecting to the bottle 110a,110b and a connection element (for example, a septum or a male luer lock fitting) in fluid connection with the spike. The spike and the connection element are located at opposite longitudinal ends of the bottle connector 130a,130b. Typically, the bottle connector 130a,130b also comprises a filtering unit (not shown in the figure) between its spike and connection element. The bottle connector 130a,130b is a disposable element for use with a single bottle 110a,110b (for example, with the spike that breaks off and remains inside the bottle 110a,110b when the bottle connector 130a, 130b is removed to prevent any accidental re-use thereof).

A transfer set 135 connects all the supply stations 105a, 105b,105c to a pressurizing unit 140 for transferring the corresponding medical fluids from the containers 110a,110b, 110c to the pressurizing unit 140. The transfer set 135 comprises a transfer line for each supply station 105a,105b, 105c. The transfer line of each supply station 105a,105b comprises a flexible tube 141a,141b that is provided (at a distal end thereof with respect to the pressurizing unit 140) with a reservoir (or drip chamber) 142a,142b and a connection element 143a,143b for mating with the connection element of the bottle connector 130a,130b. For example, the connection element 143a,143b is a spike in case the connection element of the bottle connector 130a,130b is a septum, or the connection element 143a,143b is a female luer lock fitting in case the connection element of the bottle connector 130a,130b is a male luer fitting. The reservoir 142a,142b and the connection element 143a,143b are arranged inside the bottle holder 115a,115b. The transfer line of the supply station 105c comprises a flexible tube 141c that is provided (at a distal end thereof with respect to the pressurizing unit 140) with a reservoir (or drip chamber) 142c and a spike 143c for connecting to the pouch 110c. All the flexible tubes 141a,141b,141c are coupled (at their proximal ends with respect to the pressurizing unit 140) with a T-connector 144, which comprises a plug for insertion in a corresponding port of the pressurizing unit 140. The transfer set 135 is a disposable element to be changed periodically (for example, every 12 hours).

The pressurizing unit 140 comprises an electric motor (not visible in the figure) of a peristaltic pump, which is used to pressurize the medical fluids (received from the containers 105a,105b,105c via the transfer set 135) for their injection into the patient (for example, up to a pressure of 8 bar or at a flow rate from 0.5 to 9.9 ml/s).

A delivery set 145 connects the pressurizing unit 140 to the patient for delivering the (pressurized) medical fluids thereto. The delivery set 145 comprises a delivery line made of a flexible tube 146, which is provided (at a distal end thereof with respect to the patient) with the peristaltic pump, denoted with the reference 147, to be introduced into a dedicated port provided in the pressurizing unit 140 and also to be put in fluid communication with the T-connector 144. The peristaltic pump 147 houses a rotor having a plurality of squeezing wheels, among which a corresponding portion of the flexible tube 146 is inserted. When the delivery set 145 is of single use type (not shown in the figure) for use by a single patient, the flexible tube is longer (than the flexible tube 146 shown in the figure) and it is provided (at a proximal end thereof with respect to the patient) with a connection element for mating with a connection element (for example, a plug) of a peripheral catheter (not shown in the figure), which is inserted through the skin into a peripheral vein of the patient. Instead, when the delivery set 145 is of multiple use type (as shown in the figure) for use by multiple patients, the flexible tube 146 is shorter and it is provided at the proximal end thereof with a connection element 148 for mating with a connection element 150 of an additional patient line made of a (longer) flexible tube 151 (only partially shown in the figure), which in turn ends with a connection element 152 for mating with the connection element of the peripheral catheter. The delivery set 145 is a disposable element, which in case of single use is for use entirely with a single patient and in case of multiple use is to be changed periodically (for example, every 12 hours) but with the patient line 150-152 for use with a single patient only.

A control unit 155 controls operation of the injection system 100. For example, the control unit 155 comprises a (main PCB) board with a microprocessor, a RAM that is used as a working memory by the microprocessor and a flash EPROM that stores information to be preserved even when a power supply is off (particularly, a control program of the injection system 100). Moreover, the control unit 155 comprises a touch-screen and several buttons, which are used by an operator to interact with it.

The injection system 100 is supported by a stand 160. The stand 160 is provided with wheels to facilitate moving the injection system 100; moreover, the wheels have a foot brake to secure the injection system 100 in position.

In operation, for each scan examination to be performed, the operator positions the injection system 100 close to the patient and then turns it on. If it has not already been done, the operator installs the transfer set 135 by inserting each reservoir 142a,142b and connection element 143a,143b into the corresponding bottle holder 115a,115b (across a flap thereof) and releasably blocking them therein (for example, through a snap fitting mechanism). When the pouch 110c (containing the saline solution) is not installed, the control unit 155 displays a message on its screen prompting the operator to do so. If the pouch 110c is to be used, the operator pierces a seal of the pouch 110c with the spike 143c, hangs the pouch 110c from the hook 125c and fills the reservoir 142c completely with the saline solution (by repeatedly squeezing it). At this point, the operator programs the control unit 155 by entering specific information relating to the saline solution of the pouch 110c (for example, its brand name and volume). Otherwise, if the pouch 110c is not used, the operator enters a corresponding command to the control unit 155. In both cases, when the bottle 110a (with the contrast agent) is not installed, the control unit 155 displays a message on its screen prompting the operator to do so. In response thereto, the operator takes the bottle 110a from a separate warmer (not shown in the figure), wherein the bottle 110a has been pre-warmed to a target temperature; the target temperature is set to a value high enough to allow injecting the contrast agent efficiently (for example, at the desired flow rate) and comfortably for the patient, but not too high to be harmful for the patient (for example, 32-37.5° C.). The operator pierces a seal of the bottle 110a with the spike of the bottle connector 130a. The operator then turns the bottle 110a (with the bottle connector 130a connected thereto) up-side-down, inserts the bottle connector 130a into the connection port 132a (so as to connect its connection element to the connection element 143a), mounts the protective cover 120a on the bottle holder 115a (so as to safely enclose the bottle 110a) and fills the reservoir 142a completely with the contrast agent (by repeatedly squeezing the reservoir 142a). At this point, the operator programs the control unit 155 by entering specific information relating to the contrast agent of the bottle 110a (for example, its brand name and volume). The operator repeats the same operations, if it is necessary, to install the bottle 110b (with the contrast agent or with the saline solution). The control unit 155 now displays a message on its screen prompting the operator to install the delivery set 145. In response thereto, the operator inserts the peristaltic pump 147 into the corresponding port of the pressurizing unit 140 and connects the peristaltic pump 147 to the T-connector 144. When the delivery set 145 is for multiple use, the operator further connects the connection element 150 of the patient line 150-152 to the connection element 148 of the delivery line 146-148. The operator now separately primes each transfer line 141a-143a, 141b-143b and 141c-143c by selecting a corresponding priming function on the control unit 155, so as to eliminate any air bubbles that are possibly present within the transfer lines 141a-143a, 141b-143b and 141c-143c, the delivery line 146-148 and/or the (possible) patient line 150-152. Once this priming phase has been terminated (with no air that is sensed in the injection system 100 any longer), the operator finally connects the connection element 152 (or the connection element of the delivery line in case of single use) to the connection element of the peripheral catheter (already introduced into the patient).

At this point, the operator programs the control unit 155 by entering information relating to the scan examination (for example, a gauge of the needle of the peripheral catheter, an injection profile comprising one or more phases each one defined by the type, volume and flow rate of the medical fluids, possibly selected among pre-defined injection profiles for different types of scan examinations) and then starts the scan examination. At the end of the scan examination, the operator turns the injection system 100 off, disconnects the delivery/patient line of the delivery set 145 from the peripheral catheter, and then removes and discards it.

Figure 2:
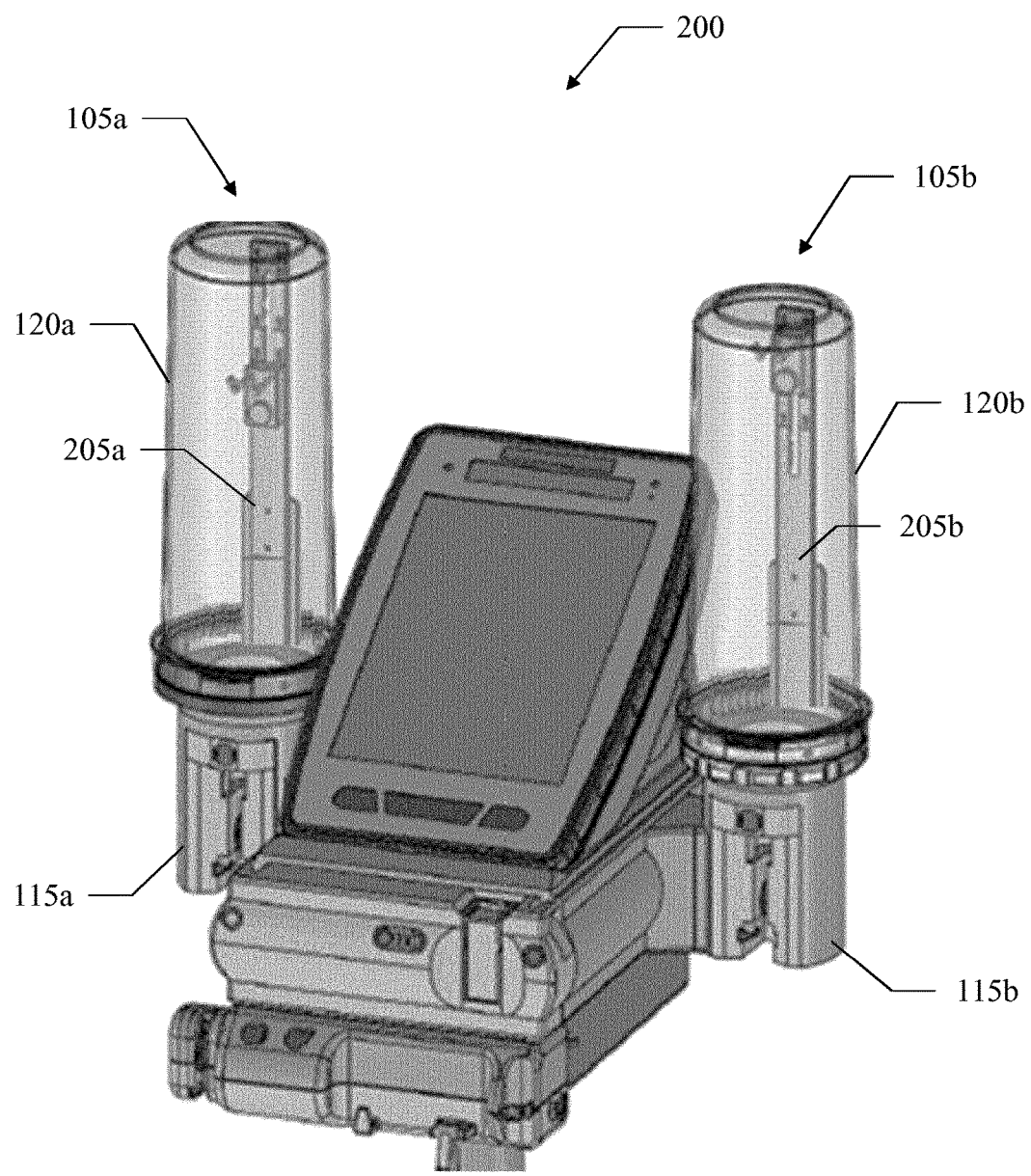
FIG. 2 shows a pictorial representation of a particular of an injection system according to an embodiment of the present disclosure.

With reference now to FIG. 2, a pictorial representation is shown of a particular of an injection system 200 according to an embodiment of the present disclosure.

The injection system 200 differs from the one described above (with respect to FIG. 1) for the addition of a bag (or pouch) holder 205a and a bag (or pouch) holder 205b in the supply station 105a and in the supply station 105a, respectively. As described in detail in the following, each bag holder 205a,205b is used to hold a bag, not shown in the figure (i.e., a soft container not self-sustaining, for example, made of polypropylene). In this case as well, the bags of the two supply stations 105a and 105b may contain a single or multiple dose of different contrast agents or of the same contrast agent, or they may contain a contrast agent and a saline solution, respectively. Each bag holder 205a,205b is configured for mounting on the bottle holder 105a,105b (instead of the protective cover 120a,120b) and for mounting the protective cover 120a,120b on it (instead of on the bottle holder 105a,105b).

The above-described solution makes the injection system 200 very versatile. Indeed, the injection system 200 may now be used with contrast agents (or saline solutions) that are provided either in bottles (not shown in the figure), as in the most common cases, or in bags, so as to reduce the costs for their shipment/storage and to facilitate their disposal, or with any combination thereof. Moreover, this result is advantageously achieved without any (significant) structural change to the injection system 200; therefore, it is possible to retrofit standard (traditional) injection systems (designed for the bottles) in a very simple and cost effective way.

Figure 3:
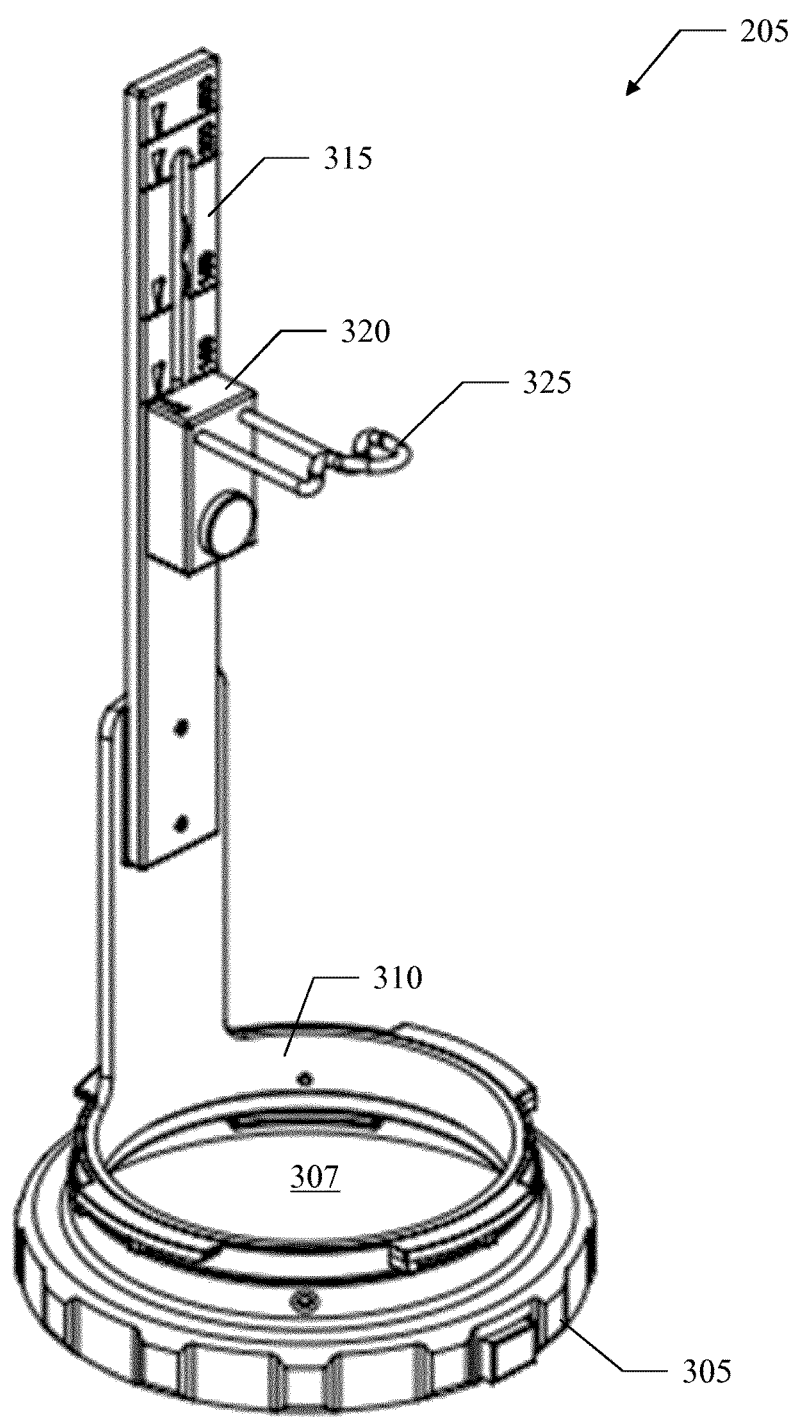
FIG. 3 shows a pictorial representation of a bag holder according to an embodiment of the present disclosure.

With reference now to FIG. 3, a pictorial representation is shown of a bag holder according to an embodiment of the present disclosure (for the sake of simplicity, hereinafter all the elements relating to the two supply stations will be denoted by removing the respective suffixes "a" and "b").

The bag holder 205 comprises a stand 305 (for example, made of polycarbonate), which is configured for mounting on the bottle holder and for mounting the protective cover on it (as described in detail in the following). For example, the stand 305 has a generically (hollow) cylindrical shape (for example, with a thickness of 0.5-1 cm); the stand 305 comprises a (lower) wider portion (for example, with a diameter of 3-5 cm and a height of 0.5-1.5 cm) and an (upper) narrower portion (for example, with a diameter of 2.5-3.0 cm and a height of 0.5-1.5 cm), which narrower portion defines a (through) opening 307 for accessing the connection port of the bottle holder, not shown in the figure. A support 310 (for example, made of steel) is formed by a crown (matching the opening 307) with a tongue extending upwards therefrom (for example, with a width of 2-4 cm and a height of 5-10 cm). The support 310 is mounted on the stand 305 with the crown of the support 310 inserted into the opening 307 (so as to be flush with the narrower portion of the stand 305, with the tongue of the support 310 projecting upwards therefrom) and then it is fixed (for example, screwed) on the stand 305. A lath 315 (for example, made of steel as well, with a width of 2-4 cm and a height of 10-20 cm) is fixed (for example, screwed) to the tongue of the support 310 so as to extend vertically upwards from the stand 305; a total height of the tongue of the support 310 plus the lath 315 is slightly lower than the one of the protective cover (not shown in the figure) for allowing its mounting thereon. A slider 320 is mounted on the lath 315; the slider 320 supports a hook 325 for hanging the bag (not shown in the figure). As described in detail in the following, the slider 320 may slide vertically along the lath 315 and it may be locked along it at different positions. The positions of the slider 320 define corresponding heights of the hook 325 for different sizes of the bag; particularly, the slider 320 may be locked at pre-defined positions (for example, four), which are labelled on the lath 315 with corresponding sizes of the bag. This further increases the versatility of the bag holder 205, since it allows its use with a number of different bags in a very simple and intuitive way.

Figure 4:
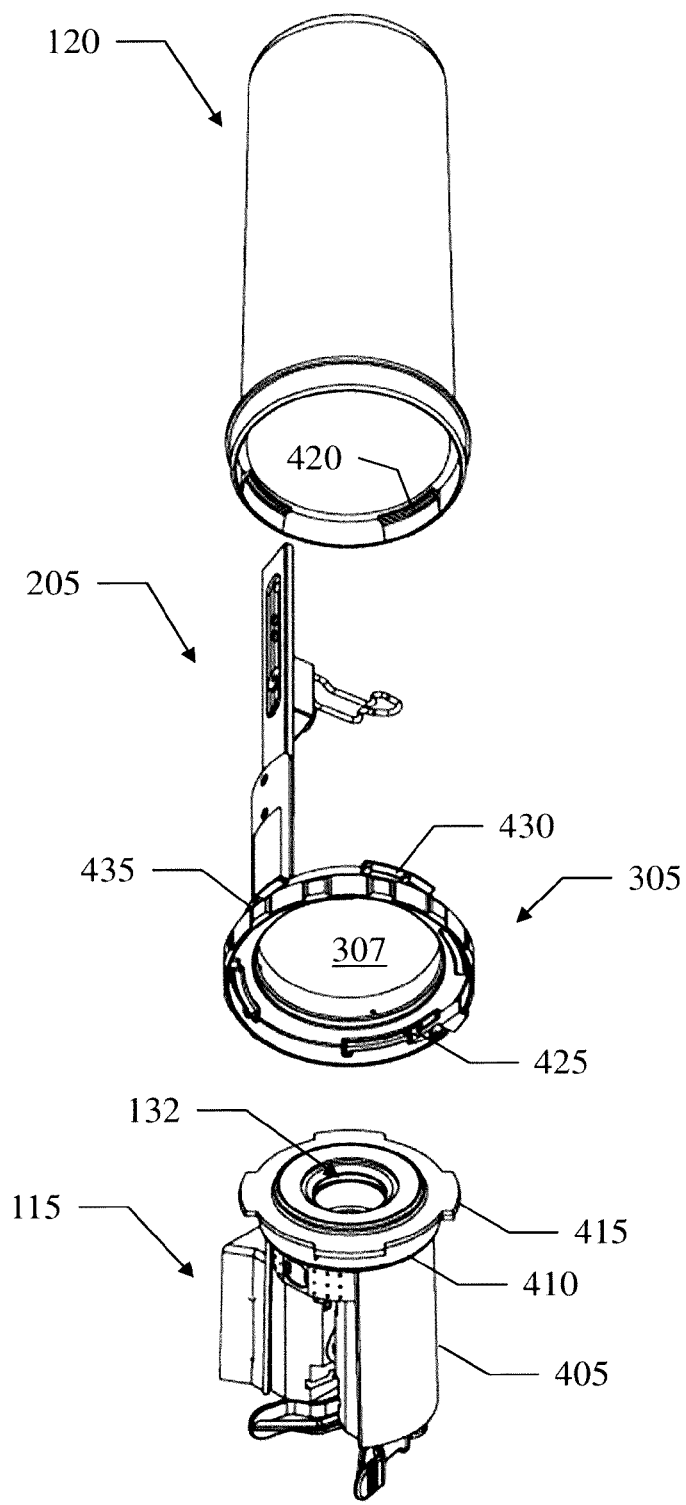
FIG. 4 shows an exemplary installation of the bag holder according to an embodiment of the present disclosure.

With reference now to FIG. 4, an exemplary installation is shown of the bag holder 205 according to an embodiment of the present disclosure.

The protective cover 120 is configured for mounting on the bottle holder 115 of a standard injection system (without the bag holder 205). For example, the bottle holder 115 and the protective cover 120 implement a bayonet-type mount. Particularly, the bottle holder 115 comprises an enclosure 405 (for example, with a generically cylindrical shape) having a lateral opening for receiving and housing the reservoir and the connection element of the corresponding transfer line (not shown in the figure). A through-hole is formed on top of the enclosure 405 to define the connection port 132 for receiving the corresponding bottle connector (not shown in the figure). A cap 410 is mounted (for example, glued or screwed) on top of the enclosure 405. The cap 410 has a through-hole matching the one of the enclosure 405, and it is provided with a male bayonet connector 415. The male bayonet connector 415 comprises a plurality of tabs (for example, four) that project radially outwards; one of the tabs is provided with a stop tooth that projects downwards from an end thereof. The protective cover 120 comprises a matching female bayonet connector 420 integral thereto. The female bayonet connector 420 comprises the same number of tabs (matching the ones of the male bayonet connector 415) that project radially inwards from a free (lower) border of the protective cover 120. The clearings that are formed between each pair of adjacent tabs of the protective cover 120 define corresponding receptors for the tabs of the male bayonet connector 415. The female bayonet connector 420 further comprises a rim that projects radially inwards along the entire protective cover 120 at an inner position. The rim is spaced apart from the tabs by a distance corresponding to a thickness of the tabs of the male bayonet connector 420, so as to define a gap for receiving them.

The protective cover 120 may be mounted on the bottle holder 115 by placing the protective cover 120 over the bottle holder 115, aligning the receptors of the female bayonet connector 420 with the tabs of the male bayonet connector 415 (dismount condition) and translating (lowering) the protective cover 120 with the receptors of the female bayonet connector 420 that slide along the tabs of the male bayonet connector 420 until the latter ones abut against the rim of the female bayonet connector 420 (interference condition). At this point, the protective cover 120 is rotated (screwed), for example, by 45°, thereby causing the tabs of the male bayonet connector 415 to enter the gaps of the female bayonet connector 420, until the stop tooth of the male bayonet connector 415 (arranged upstream the corresponding tab along a rotation direction) abuts against one of the tabs of the female bayonet connector 420 (mount condition). The same operations are repeated in reverse order to remove the protective cover 120 from the bottle holder 115.

In the solution according to an embodiment of the present disclosure, the bag holder 205 is mounted on the bottle holder 115 (instead of the protective cover 120). For this purpose, the stand 305 is provided with a female bayonet connector 425 similar to the female bayonet connector 420. In this case, the wider portion of the stand 305 is provided with the same number of tabs that project radially inwards from a free (lower) border thereof. The narrower portion of the stand 305 forms an abutment spaced apart from the tabs of the wider portion of the stand 305 by a distance corresponding to the thickness of the tabs of the male bayonet connector 415, so as to define a similar gap for receiving them. Moreover, the stand 305 is provided with a male bayonet connector 430 substantially the same as the male bayonet connector 415 (i.e., comprising the same number of tabs that project radially outwards, with one of the tabs that is provided with a stop tooth that projects downwards from an end thereof). The bag holder 205 is mounted on the bottle holder 115 with the female bayonet connector 425 that now mates with the male bayonet connector 415 (i.e., by translating and then rotating it). In order to facilitate this operation, the wider portion of the stand 305 is also shaped externally with a series of radial projections 435 increasing the grip of the hand of the operator thereon. As a result, the protective cover 120 may be mounted on the bag holder 205 exactly in the same way as on the bottle holder 115 (with the female bayonet connector 420 that now mates with the male bayonet connector 430).

In this way, the injection system with the bag holder 205 stays compatible with previous injection systems without it.

Figure 5A:
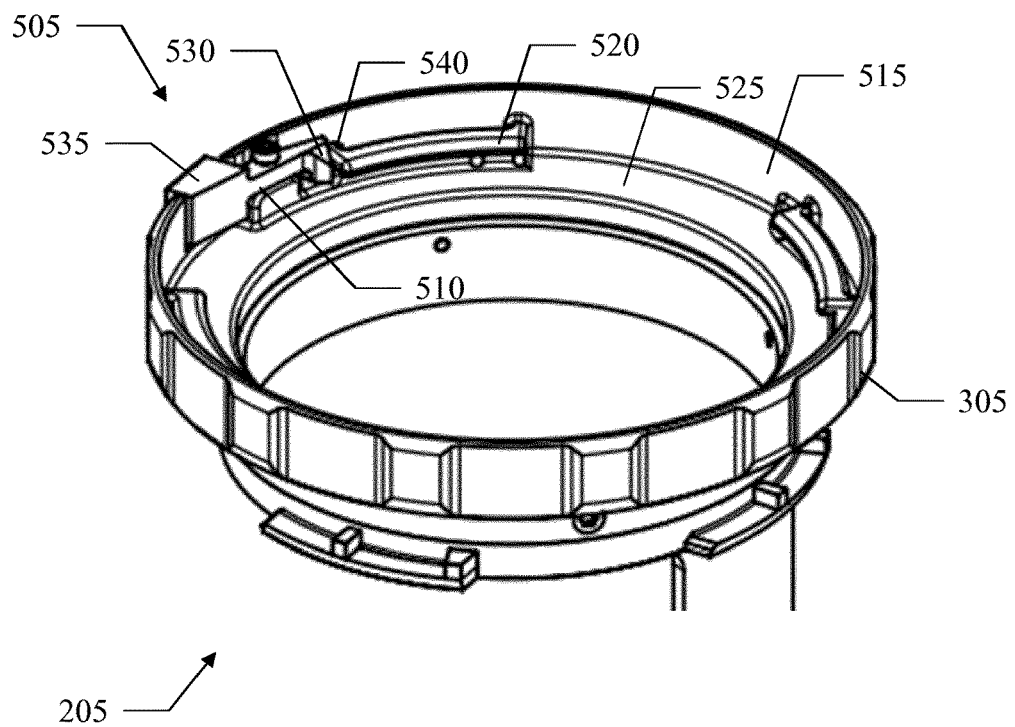
FIG. 5A-FIG. 5B show a pictorial representation of different details of the bag holder according to an embodiment of the present disclosure.
Figure 5B:
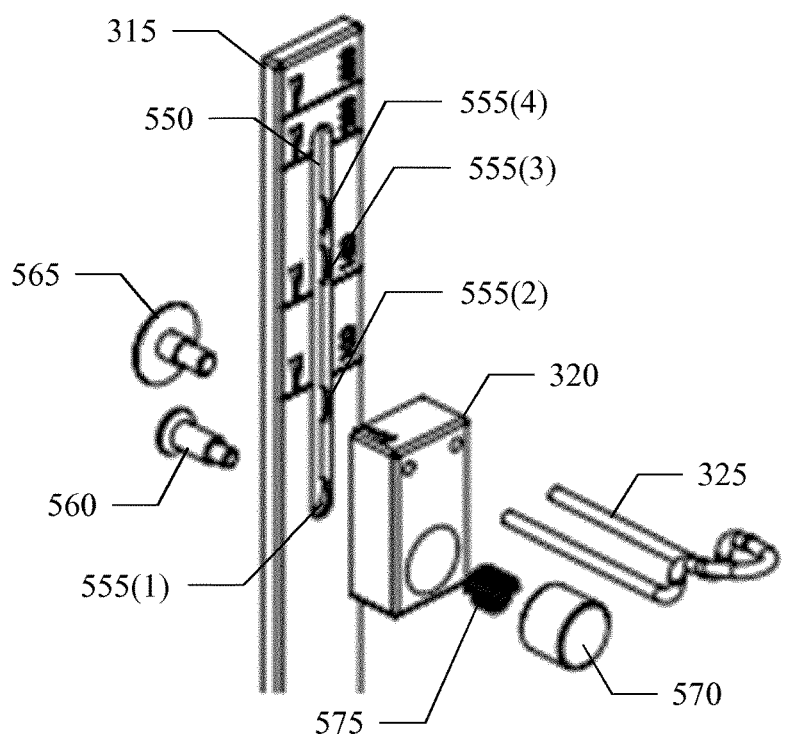

With reference now to FIG. 5A-FIG. 5B, a pictorial representation is shown of different details of the bag holder 205 according to an embodiment of the present disclosure.

Particularly, FIG. 5A shows a partial bottom view of the bag holder 205. In the solution according to an embodiment of the present disclosure, the bag holder 205 comprises a locking mechanism 505 that may be switched between a locking condition (for locking the bag holder 205 on the bottle holder, not shown in the figure) and an unlocking condition (for unlocking it therefrom).

The locking mechanism 505 is formed by a lever 510 that is arranged inside the stand 305. The lever 510 runs along a lateral surface 515 of the wider portion of the stand 305, adjacent to one of the tabs of its female bayonet connector, denoted with the reference 520 (upstream along a rotation direction of the bag holder 205 for mounting on the bottle holder, counterclockwise in the example at issue). The lever 510 is hinged at its center to a peg projecting perpendicularly from the abutment of the wider portion of the stand 305, denoted with the reference 525, so as to be free to pivot in parallel thereto. An end of the lever 510 proximal to the tab 520 is provided with a lead-in tooth 530 extending inwards; another end of the lever 510 distal from the tab 520 is instead provided with a push-button 535 extending outwards, which faces a corresponding window opened in the lateral surface 515. A spring 540 is arranged between the lateral surface 515 and the proximal end of the lever 510. In a rest condition, the spring 540 biases the lever 510 to a locking position wherein it faces the tab 520 and then the push-button 535 projects outside the stand 305 across the corresponding window of the lateral surface 515.

The lever 510 (with its lead-in tooth 530) and the spring 540 implement a pawl of a ratchet formed when they interact with the male bayonet connector of the bottle holder, with the push-button 535 that implements a corresponding release mechanism. Particularly, during the mounting of the bag holder 205 on the bottle holder, when the bag holder 205 is rotated (counterclockwise) a tab of the male bayonet connector reaches the lead-in tooth 530 thereby pushing it inwards against the spring 540 so as to allow its passage. Once this tab of the male bayonet connector has passed the lead-in tooth 530 (entering the gap between the tab 520 and the abutment 525), it clears the lead-in tooth 530 so that the spring 540 returns the lever 510 with a snap to its locking position. In this condition, the male bayonet connector (and then the whole bottle holder) is locked between the stop tooth of the female bayonet connector (not shown in the figure) and the lever 510 (which prevents its unscrewing). As a result, the bag holder 205 is secured on the bottle holder in a safe way; this is achieved automatically (in a snap way) during the mounting of the bag holder 205 without requiring any manual intervention.

When the bag holder 205 has to be removed from the bottle holder, the operator presses the push-button 535 with a finger, so as to cause the proximal end of the lever 510 to move inwards until it abuts against the lateral surface 515; as a result, the lever 510 reaches an unlocking position wherein it clears the tab 520. In this condition, the operator may rotate the stand 305 in the opposite direction (i.e., clockwise), by gripping the stand 305 externally with the hand, thereby causing the tabs of the male bayonet connector to leave the gaps of the female bayonet connector (with the push-button 535 that may be released since the lever 510 is now maintained in the unlocking position by the tab of the male bayonet connector that has left the gap between the tab 520 and the abutment 525). Once the tabs of the male bayonet connector have reached the receptors of the female bayonet connector, the operator may pull out the bag holder 205 from the bottle holder. In this way, the operation is very easy and it may be performed manually without any tool.

Moving to FIG. 5B, a partial exploded view is shown of the bag holder 205. As mentioned above, the slider 320 (with the hook 325) may slide along the lath 315.

In the solution according to an embodiment of the present disclosure, for this purpose a (longitudinal) slotted-hole 550 is formed along the lath 315 (vertically). Four (transversal) recesses are provided along the slotted-hole 550, so as to define corresponding (enlarged) through-holes for the pre-defined positions of the slider 320; particularly, a through-hole 555(1) is formed at a lower end of the lath 315 (proximal to the stand of the bag holder 205, not shown in the figure), a through-hole 555(4) is formed close to an upper end of the lath 315 (distal from the stand of the bag holder 205) at a distance thereof corresponding to a length of the slider 320, and other two through-holes 555(2),555(3) are formed between the through-hole 555(1) and the through-hole 555(4).

The slider 320 is mounted on the lath 315 with two (cap) screws 560 and 565. Particularly, the screw 560 has a head larger than the through-holes 555(1)-555(4) and a shank with a (thinner) distal portion (with respect to the head) matching the slotted-hole 550 and a (larger) proximal portion matching the through-holes 555(1)-555(4). The screw 565 has a head larger than the through-holes 555(1)-555(4) and a shank matching the slotted-hole 550. The screw 560 is inserted from the back of the lath 315 into a (current) one of the through-holes 555(1)-555(4) and it is screwed into a corresponding threaded hole of a push-button 570 of the slider 320, with a spring 575 interposed between them; the screw 565 is inserted from the back of the lath 315 into the slotted-hole 550 and it is screwed into a corresponding threaded hole of the slider 320.

The shank of the screw 565 maintains the slider 320 aligned with the lath 315 (without interfering with its sliding). In a rest condition, the spring 575 biases the screw 560 to a locking position wherein the larger portion of its shank is arranged in the current through-hole 555(1)-555(4). In this condition, the larger portion of the shank of the screw 560 prevents its sliding along the (narrower) slotted-hole 550, so as to lock the slider 320 in the corresponding pre-defined position. The operator may move the slider 320 to another pre-defined position by pressing the push-button 570 with a finger, so as to cause the narrower portion of the shank of the screw 560 to enter the current through-hole 555(1)-555(4) against the spring 575. As a result, the screw 560 reaches an unlocking position wherein the narrower portion of its shank may now slide along the slotted-hole 550. The operator then moves the slider 320 along the lath 315 (with the push-button 570 that may be released since it is maintained pressed by the interference of the larger portion of the shank of the screw 560 with the slotted-hole 550). Particularly, the operator moves the slider 320 so as to bring the shank of the screw 560 to the through-hole 555(1)-555(4) of the desired pre-defined position, upwards at most until the shank of the screw 565 abuts against the distal end of the slotted-hole 550, with the shank of the screw 560 at the through-hole 555(4), or downwards at most until the shank of the screw 560 abuts against the proximal end of the slotted-hole 550, at the through-hole 555(1). As soon as the shank of the screw 560 reaches one of the through-holes 555(1)-555(4) with the push-button 570 that is not pressed any longer, the spring 575 returns the screw 560 to its locking position (with the larger portion of the shank of the screw 560 that enters this through-hole 555(1)-555(4) thereby preventing its sliding).

In this way, the bag holder 205 may be adapted to bags with different sizes in a very fast way with simple manual operations (without any tool).

Figure 6A:
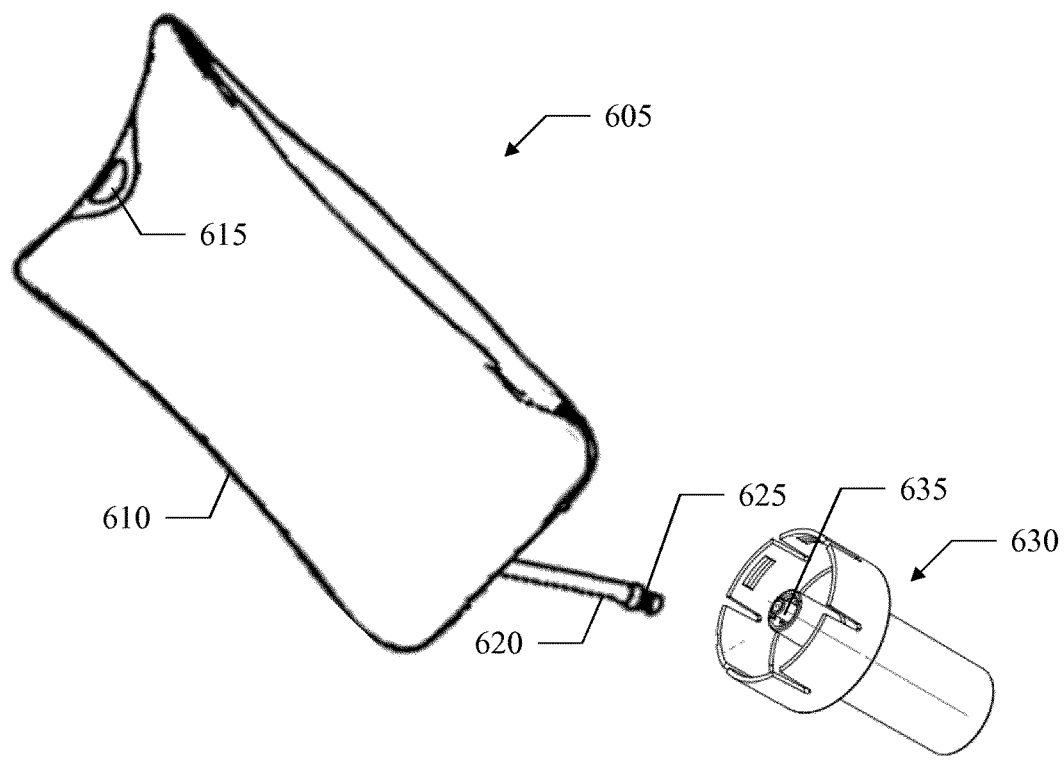
FIG. 6A-FIG. 6B show a pictorial representation in front view and in back view, respectively, of an exemplary connection scheme according to an embodiment of the present disclosure.
Figure 6B:
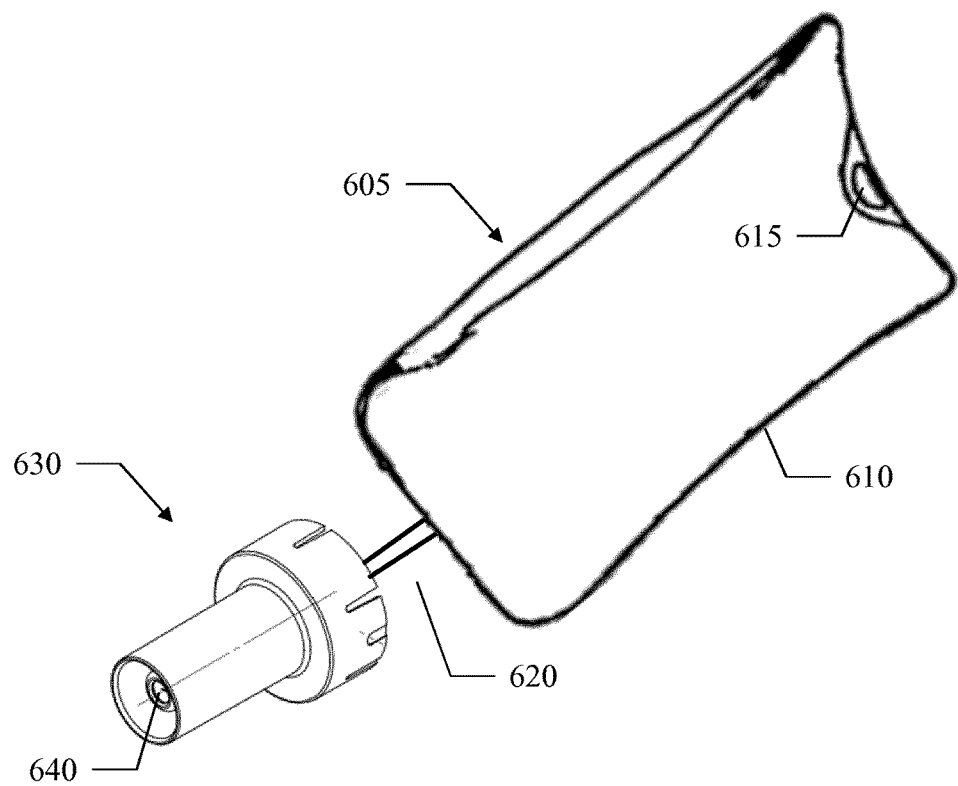

With reference now to FIG. 6A-FIG. 6B together, a pictorial representation is shown in front view and in back view, respectively, of an exemplary connection scheme according to an embodiment of the present disclosure.

Particularly, each bag (or pouch), denoted with the reference 605, comprises a (soft) container 610 for containing a medical fluid, for example, a contrast agent. The container 610 is provided at a longitudinal end thereof with a handle 615 for hanging it. A (small) tube 620, in fluid communication with the container 610, projects outwards from its longitudinal end opposite the handle 615 for delivering the medical fluid. A free end of the tube 620 is equipped with a connection element 625, for example, a female luer fitting (only visible in FIG. 6A).

A bag connector 630 is provided for connecting the bag 605 to the corresponding transfer line. The bag connector 630 has a generically cylindrical shape, with a (prevalent) narrower portion and a (residual) wider portion. The bag connector 630 comprises a connection element 635 at a free end of its wider portion, for example, a male luer fitting (only visible in FIG. 6A), for connecting to the connection element 625. The bag connector 630 further comprises a connection element 640 at a free end of its narrower portion, for example, a septum or a male luer lock fitting (only visible in FIG. 6B), for connecting to the transfer line. The connection element 635 and the connection element 640 are in fluid communication between them. The bag connector 630 may also comprise a filtering unit (not shown in the figure) between its connection elements 635 and 640. The bag connector 630 is a disposable element for use with a single bag 605.

When the bag 605 has to be used, the operator connects the bag connector 630 to the bag 605 (by mating the connection element 625 with the connection element 635). The operator then hangs the bag 605 (with the bag connector 630 connected thereto) from the hook of the bag holder (not shown in the figure) by means of its handle 615. At this point, the operator inserts the bag connector 630 into the connection port of the bottle holder (not shown in the figure) across the opening of the bag holder, so as to connect its connection element 640 to the corresponding connection element of the transfer line.

The bag connector 630 avoids any spilling of the medical fluid contained in the bag 605, and then any contamination of the bag holder.

Figure 7:
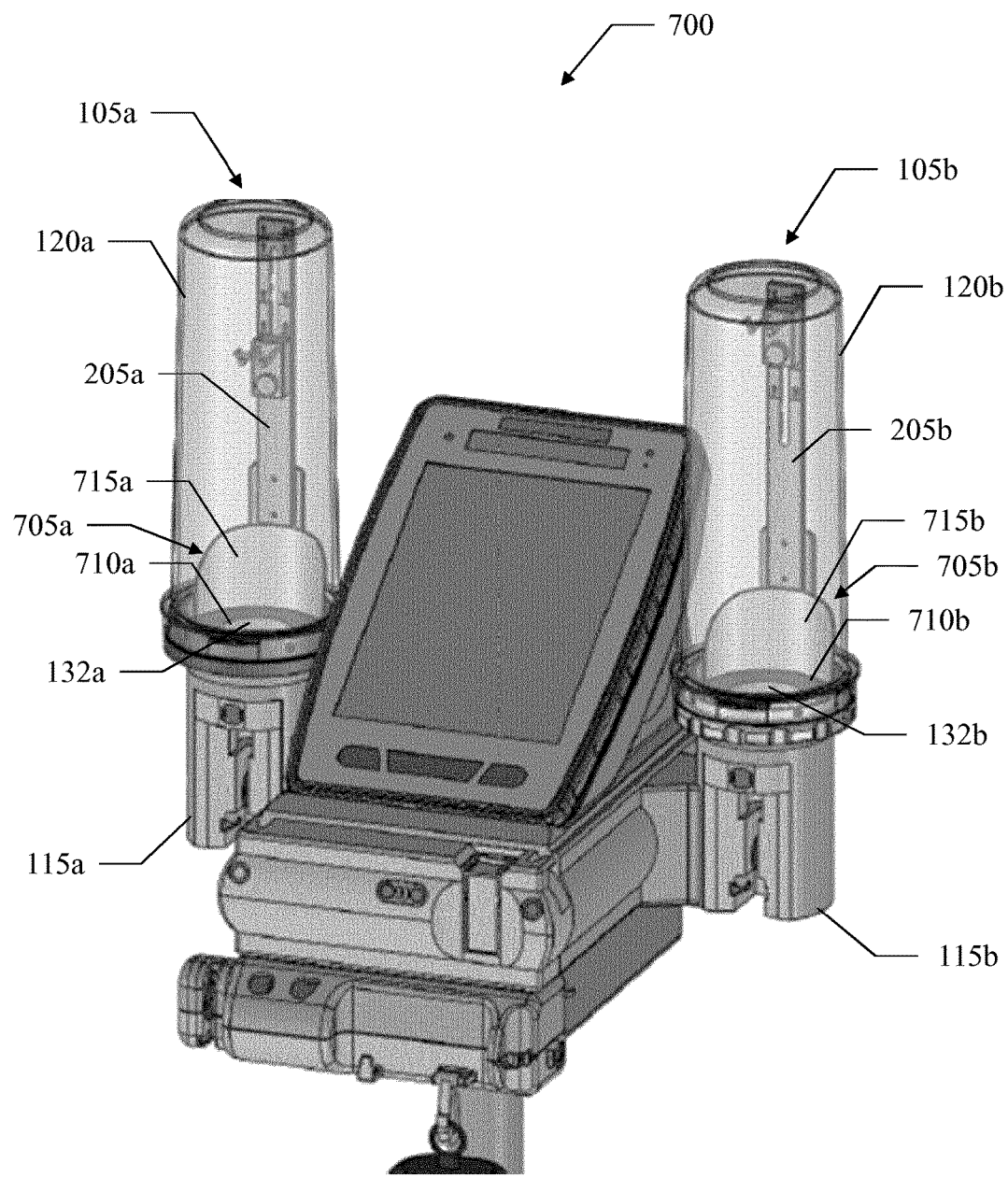
FIG. 7 shows a pictorial representation of a particular of an injection system according to another embodiment of the present disclosure.

With reference now to FIG. 7, a pictorial representation is shown of a particular of an injection system 700 according to another embodiment of the present disclosure.

The injection system 700 differs from the one described above (with reference to FIG. 2) for the addition of a heating device 705a and a heating device 705b in the supply station 105a and in the supply station 105b, respectively. Each heating device 705a,705b is arranged inside a chamber defined by the protective cover 120a,120b mounted on the bag holder 205a,250b (in turn mounted on the bottle holder 115a,115b) to maintain the medical fluid contained in the bags (not shown in the figure) at the target temperature.

In the solution according to an embodiment of the present disclosure, the heating device 705a,705b comprises two distinct heating elements (for example, implemented by corresponding resistors). Particularly, a (first) heating element 710a,710b extends around the connection port 132a,132b and a (second) heating element 715a,715b extends transversally to the heating element 710a,710b.

The above-described configuration of the heating device 705a,705b significantly improves its performance. Particularly, this allows maintaining the medical fluid at the target temperature efficiently (with higher uniformity and lower power consumption).

Figure 8A:
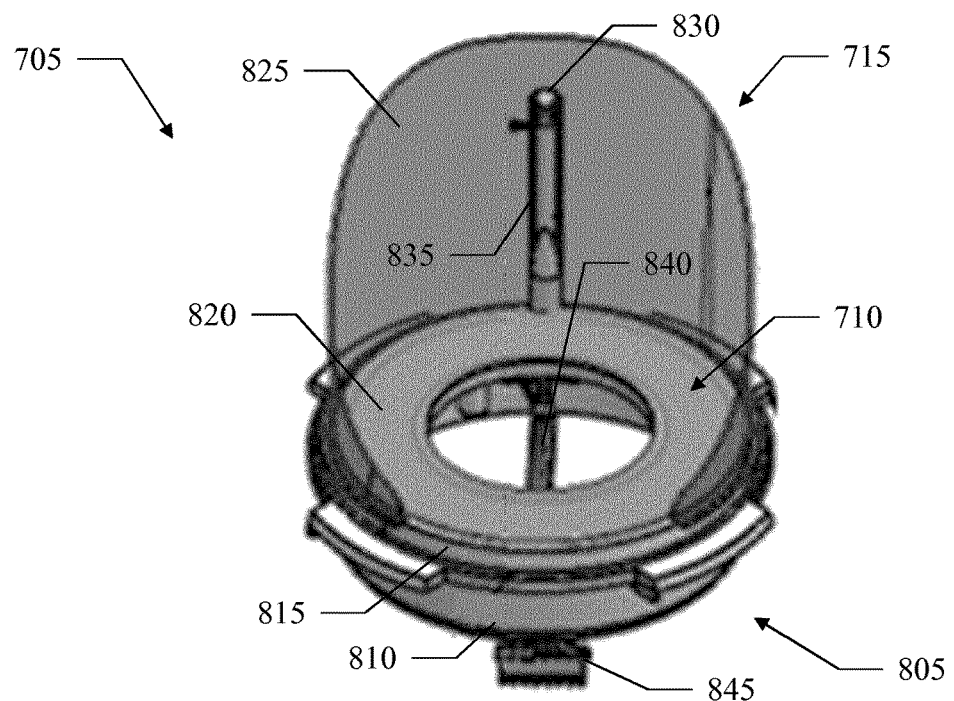
FIG. 8A-FIG. 8B show a pictorial representation in top view and in bottom view, respectively, of a heating device according to an embodiment of the present disclosure.
Figure 8B:
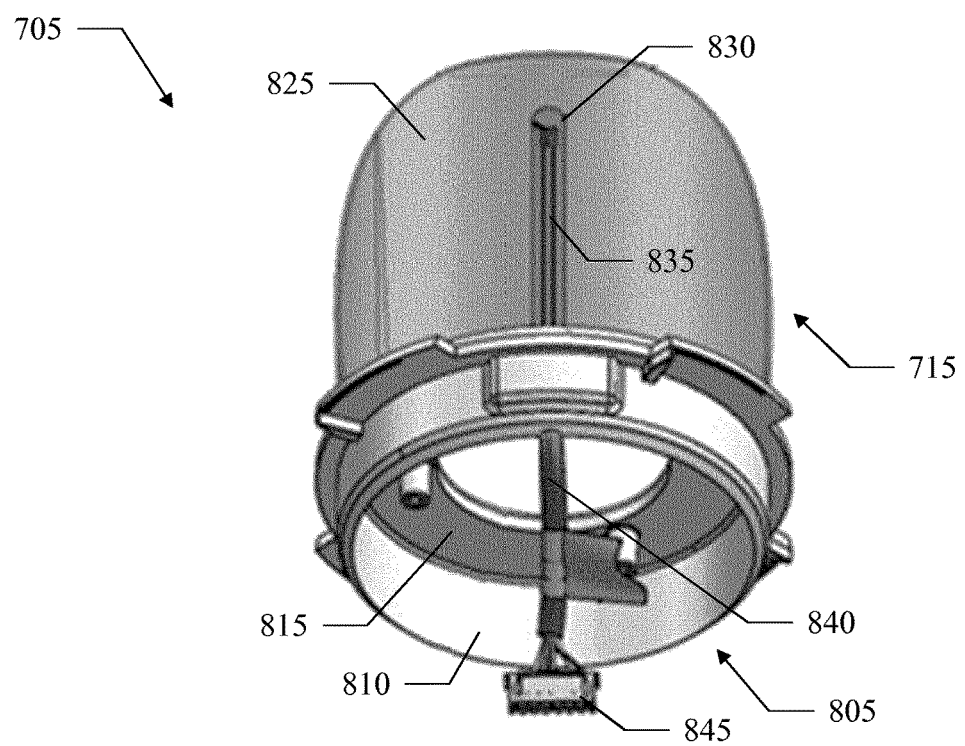

With reference now to FIG. 8A-FIG. 8B together, a pictorial representation is shown in top view and in bottom view, respectively, of a heating device according to an embodiment of the present disclosure (for the sake of simplicity, hereinafter all the elements relating to the two supply stations will be denoted again by removing the respective suffixes "a" and "b").

The heating device 705 comprises a stand 805 (for example, made of polycarbonate). As described in the following, the stand 805 is configured for mounting on the bottle holder and for mounting the protective cover or the bag holder (not shown in the figure) on it, instead of on the bottle holder. For example, the stand 805 comprises a crown 810, which is shaped generically as a hollow cylinder (for example, with a diameter of 3-5 cm, a height of 0.5-1.5 cm and a thickness of 0.5-1 cm). The crown 810 is open at its lower end, whereas it is closed at its upper end by a (flat) ring 815 (for example, having a thickness of 0.5-1 cm). The ring 815 is defined by a disk with a through-hole opened at the center thereof, which through-hole matches the connection port of the bottle holder (for example, with a diameter of 1.5-2.5 cm).

The heating element 710 (only visible in FIG. 8A) comprises a ring 820 of electrical insulating material (for example, polycarbonate), and it is hereinafter referred to as ring heater 710. The ring 820 is flat (i.e., with a dimension far lower than the other ones, for example, with a thickness of 0.3-0.7 cm and a diameter of 3-5 cm). The ring 820 matches the ring 815 (i.e., it is defined by a disk with a corresponding through-hole opened at the center thereof). The ring 820 is fixed (for example, glued) on the ring 815, and more specifically within a corresponding seat (defined by a depression extending from an upper surface of the ring 815) so as to be flush with it (horizontally in an operative condition). A positioning notch is formed at an outer border of the ring 820 matching a reference tooth provided in the seat of the ring 815 to ensure a correct alignment of the ring 820.

The heating element 715 comprises a thin fin 825 (for example, with a thickness of 0.3-0.7 cm) of electrical insulating material (for example, polycarbonate), and it is hereafter referred to as fin heater 715. The fin 825 has a plan development with a (lower) base (for example, with a length of 7-10 cm) and a rounded, dome-shaped (upper) profile (for example, with a height ranging from 2-5 cm at the center to 0.1-0.5 cm at the ends of the base). A tab (not visible in the figure) extends downwards at the center of the base (for example, with a height of 0.4-0.6 cm and a width of 0.6-1.0 cm). The fin 825 is curved (along its base) to match a (circumferential) outline of the ring 820. The fin 825 is shorter than the outline of the ring 820; therefore, the fin 825 (once curved) extends along a circular arc subtending an angle lower than 360°, for example, equal to 220°-340°, preferably 240°-320° and still more preferably 260°-300°, such as 280°. The fin 825 is mounted on the stand 805 (vertically in an operative condition) with its base inserted into a corresponding groove provided in the upper surface of the ring 815 (adjacent to the ring 820) and with its tab inserted in a corresponding seat provided in a lateral surface of the crown 810, and then it is fixed (for example, glued) thereon.

The specific arrangement of the (ring and fin) heaters 710,715 described above further improves their performance.

One or more temperature sensors 830 (for example, a main one and a redundant one) are fixed on the fin 825, close to an apex thereof. For example, the temperature sensors 830 are placed on an inner surface of the fin 825 that faces the bag or the bottle (not shown in the figure) in an operative condition. The temperature sensors 830 are soldered at a free end of corresponding (electrically) connection tracks 835 (for example, made of copper) that extend vertically along the fin 825 on an outer surface thereof. A cabling (or wiring) system 840 (for example, galvanically insulated by opto-couplers to avoid ground loops) electrically connects the ring heater 710, the fin heater 715 and the connection tracks 835 (and then the sensors 830) to an electrical connector 845.

Figure 9:
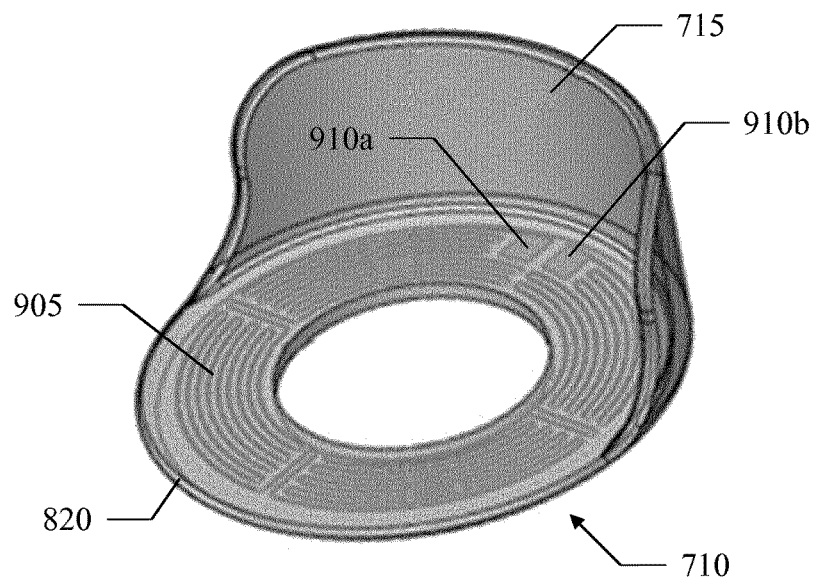
FIG. 9 shows a pictorial representation of a heating element according to an embodiment of the present disclosure.

With reference now to FIG. 9, a pictorial representation is shown of the ring heater 710 according to an embodiment of the present disclosure.

The ring heater 710 (shown in combination with the fin heater 715) comprises a heating coil 905, which is formed by a resistor embedded in the ring 820 for generating heat by the Joule effect. The heating coil 905 is made of an (electrical) resistive material (for example, nickel-chrome). The heating coil 905 has a resistance preferably of 30-200Ω, more preferably of 50-150Ω and still more preferably of 80-120Ω, such as 100Ω. For example, the heating coil 905 is formed by a track that is arranged in four sectors, in each one of them extending along two-way concentric arcs. Each sector is connected to the adjacent one via a two-way radial segment. The heating coil 905 ends (in an outer portion of two adjacent sectors) with two pads 910a and 910b, which are exposed on a lower surface of the ring 820 for connecting the heating coil 905 electrically to the cabling system (not shown in the figure).

Figure 10:
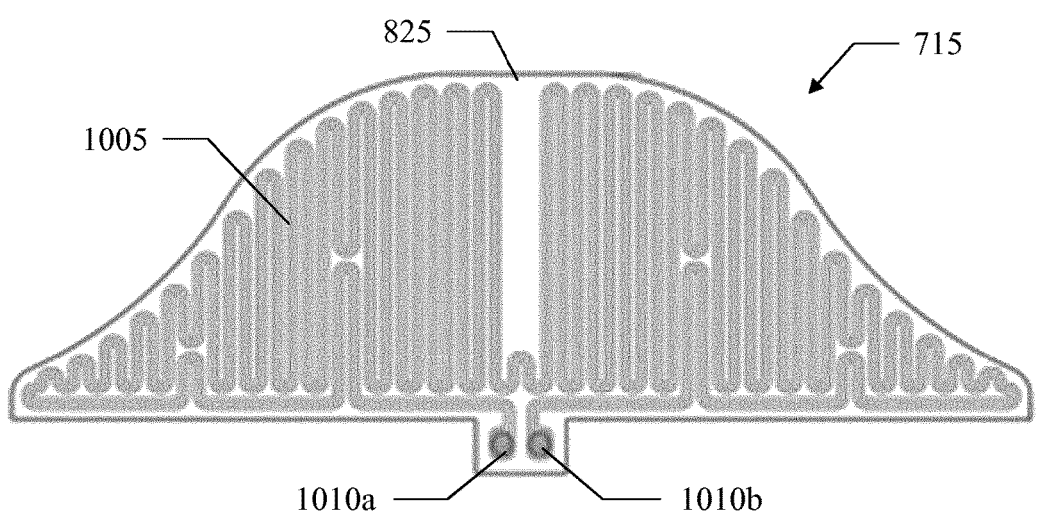
FIG. 10 shows a pictorial representation of another heating element according to an embodiment of the present disclosure.

With reference now to FIG. 10, a pictorial representation is shown of the fin heater 715 according to an embodiment of the present disclosure.

In this case as well, the fin heater 715 comprises a heating coil 1005, which is formed by a resistor embedded in the fin 825 for generating heat by the Joule effect. The heating coil 1005 is made of an (electrical) resistive material (for example, again nickel-chrome). The heating coil 1005 has a higher resistance, for example, equal to preferably 2-8 times, more preferably 3-7 times and still more preferably 4-6 times, such as 5 times the resistance of the ring heater, not shown in the figure (for example, preferably 300-700Ω, more preferably 400-600Ω and still more preferably 450-550Ω, such as 500Ω). For example, the heating coil 1005 is formed by a track that extends along the base of the fin 825 with some peaks of decreasing height moving towards its ends and then along two-way vertical segments, leaving a portion of the fin 825 free in correspondence to the temperature sensors and the corresponding connection tracks (not shown in the figure). The heating coil 1005 ends (in the tab of the fin 825) with two pads 1010a and 1010b, which are exposed on an inner surface of the fin 825 for connecting the heating coil 1005 electrically to the cabling system (not shown in the figure).

The above-described structure of the (ring and fin) heaters is simple, but at the same time very effective.

Figure 11:
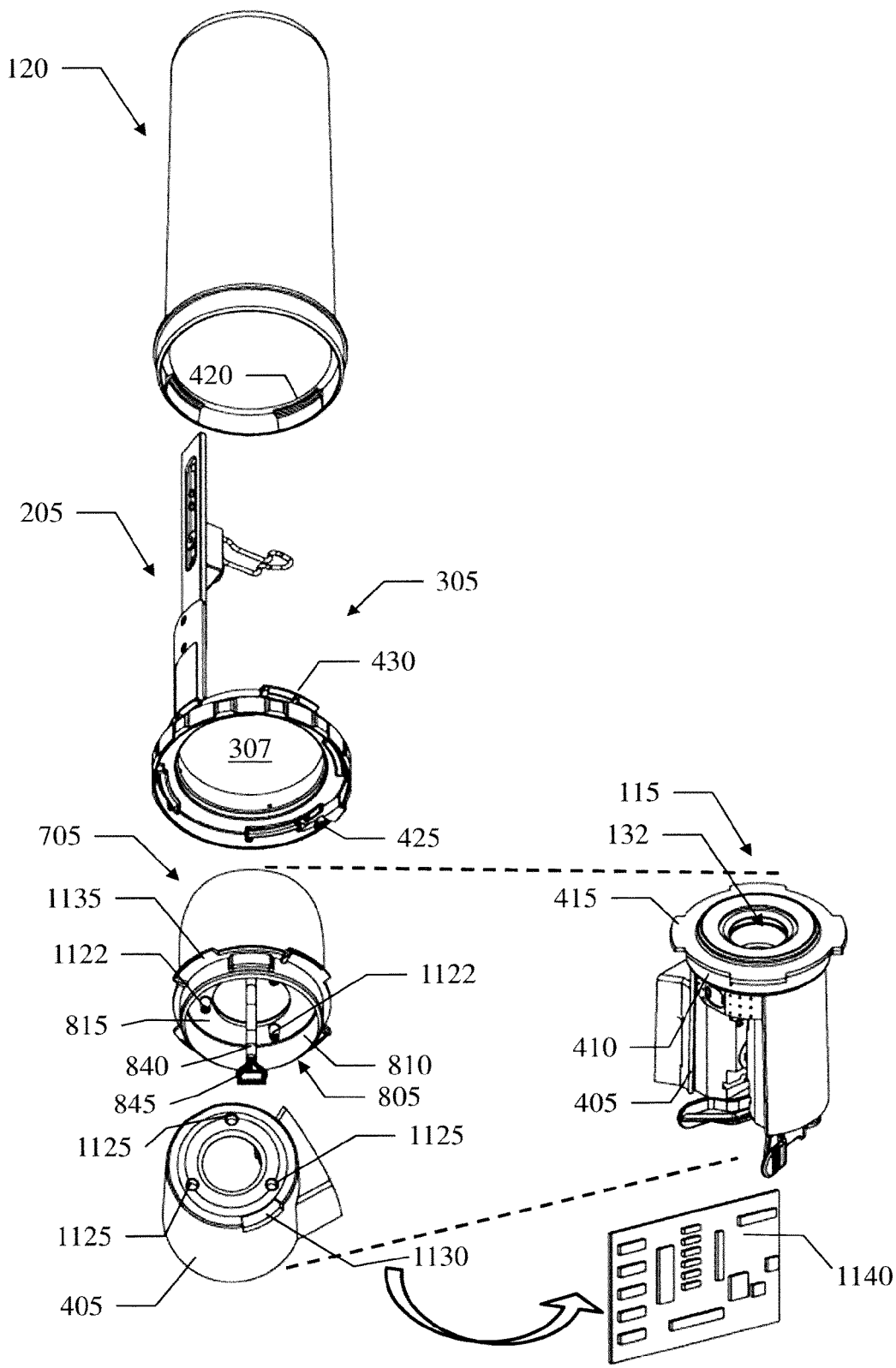
FIG. 11 shows an exemplary installation of the heating device according to an embodiment of the present disclosure.

With reference now to FIG. 11, an exemplary installation is shown of the heating device 705 according to an embodiment of the present disclosure.

In the solution according to an embodiment of the present disclosure, the heating device 705 replaces the cap 410. For this purpose, the stand 805 is provided with a plurality of pegs 1122, for example, three (only two visible in the figure) that project downwards from the ring 815. The pegs 1122 match corresponding holes 1125 that are already provided on top of the enclosure 405 (for receiving similar pegs of the cap 410, not visible in the figure). Moreover, a window 1130 is opened at the top of the enclosure 405 for inserting the electrical connector 845 and a corresponding portion of the cabling system 840. The crown 810 is provided with a male bayonet connector 1135 substantially the same as the male bayonet connectors 415 and 430 (i.e., comprising the same number of tabs that project radially outwards, with one of the tabs that is provided with a stop tooth that projects downwards from an end thereof). The heating device 705 is mounted on the enclosure 405 (without the cap 410) by passing the electrical connector 845 through the window 1130 and then plugging it into a corresponding connector (not shown in the figure), which is (electrically) connected to a controller 1140 of the heating device 705 (for example, housed in the control unit of the injection system, not shown in the figure). For example, the controller 1140 is implemented with a (daughter PCB) board mounting a microprocessor, a RAM that is used as a working memory by the microprocessor and a flash EPROM that stores information to be preserved even when a power supply is off (particularly, a control program of the heating device 705). At this point, the heating device 705 is fitted on top of the enclosure 405 and fixed thereto (for example, glued or screwed as above). As a result, when the bag holder 205 is not used, the protective cover 120 may be mounted on the heating device 705 exactly in the same way as on the bottle holder 115 with the cap 410 (with the female bayonet connector 420 that now mates with the male bayonet connector 1135). Alternatively, the bag holder 205 may be fitted on the heating device 705 (which slides across its opening 307) and then mounted thereon exactly in the same way as on the bottle holder 115 with the cap 410 (with the female bayonet connector 425 that now mates with the male bayonet connector 1135).

In this way, the injection system with the heating device 705 stays compatible with previous injection systems without it (with or without the bag holder 205).

In operation, the controller 1140 supplies the heating device 705 (for example, at 20-40V). The controller 1140 continually monitors the temperatures measured by both the main temperature sensor and the redundant temperature sensor of the heating device 705 (for safety reasons). If the difference between the measured temperatures exceeds a threshold value (for example, 0.3-1° C.) for two (or more) consecutive measures (to improve robustness), the controller 1140 enters an error condition (for example, by sending an error message to the control unit of the injection system, causing it to stop operation of the injection system and to provide a warning message to the operator). Otherwise, the controller 1140 drives the heating device 705 with hysteresis (to reduce a frequency of its switching). Particularly, assuming that at the beginning the temperature measured by the main temperature sensor is lower than the target temperature minus a delta temperature (for example, 0.5-1 2° C.), the controller 1140 switches the heating device on. For this purpose, the controller 1140 may control the ring heater and the fin heater either individually or together. For example, the controller 1140 may generate a (common) control signal corresponding to the difference between the target temperature and the measured temperature, which control signal is translated to a same PWM power signal that directly drives both the ring heater and the fin heater. As indicated above, the resistance of the fin heater is higher than the resistance of the ring heater, so that the fin heater converts more electric power into heat than the ring heater does (for example, 10-12 W and 2-4 W, respectively, when they are driven by a same current of 0.3-0.7 mA). The difference heating provided by the ring heater and the fin heater further improves the performance of the heating device. At the same time, the controller 1140 starts verifying whether the measured temperature exceeds the target temperature plus the same delta temperature. As soon as this occurs, the controller 1140 switches the heating device off. At this point, the controller 1140 starts verifying whether the measured temperature falls below the target temperature minus the delta temperature. As soon as this occurs, the controller 1140 switches the heating device on again, so as to repeat the same operations continually. As a result, the temperature in the chamber formed between the bottle holder 115 and the protective cover 120 swings around the target temperature in a range defined by the delta temperature.

MODIFICATIONS

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides an injection system. However, the injection system may be of any type (for example, with another pressurizing system, with a ceiling mount for mounting it on the ceiling of an imaging suite).

In an embodiment, the injection system is for injecting one or more fluids into a patient. However, the fluids may be in any number and of any type (for example, whatever medical fluid to be used in a generic medical application for diagnostic or therapeutic purposes, such as a drug or a body fluid, or more generally to be used in any other treatment, such as for cosmetic purposes); moreover, the fluid may be injected in any way (for example, intra-arterially) into any (human or animal) patient.

In an embodiment, the injection system comprises one or more supply stations each one for supplying one of the fluids to be injected. However, the injection system may comprise any number of supply stations (down to a single one) for supplying the same or different fluids (in any combination).

In an embodiment, at least one of the supply stations comprises a bottle holder for holding a bottle containing the fluid to be injected. However, the solution detailed in the following may be applied to any number of supply stations (from a single one to all of them), for example, with a supply station (or more) without the bag holder for using the bottle and/or a supply station (or more) with the bag holder for using the bag; moreover, the bottle holder may be of any type (for example, with a mechanical lock for the bottle) and it may be used to hold a bottle of any type (for example, made of rigid plastic) and size.

In an embodiment, the bottle holder comprises a first connector. However, the first connector may be of any type (for example, for a snap fitting, a screw fastening).

In an embodiment, said at least one supply station comprises a cover for covering the bottle when held on the bottle holder. However, the cover may be of any type, shape and size (for example, a cap hinged to the bottle holder); moreover, the cover may cover the bottle in any way (for example, enclosing the bottle completely or only partially).

In an embodiment, the cover comprises a second connector for mating with the first connector to mount the cover on the bottle holder (see above).

In an embodiment, said at least one supply station further comprises a bag holder for holding a bag containing the fluid to be injected. However, the bag holder may be of any type (for example, with a seat for the bag); moreover, it may be used to hold a bag of any type (for example, made of polyethylene) and size.

In an embodiment, the bag holder comprises a further second connector for mating with the first connector (to mount the bag holder on the bottle holder) and a further first connector for mating with the second connector (to mount the cover on the bag holder). However, the further first connector and/or the further second connector may be exactly the same or simply compatible with the first connector and the second connector, respectively.

In an embodiment, the injection system comprises a delivery arrangement for delivering the fluids to the patient. However, the delivery arrangement may be of any type (for example, with individual transfer lines for each supply station, with a delivery line ending with a needle for direct insertion into the patient).

In an embodiment, the bottle holder comprises a connection port for connecting the bottle to the delivery arrangement. However, the connection port may be of any type, shape, size (for example, a valve integral with the bottle holder) and it may be arranged at any position (for example, laterally).

In an embodiment, the bag holder comprising an opening for accessing the connection port to connect the bag to the delivery arrangement in the connection port across the opening. However, the opening may have any shape (for example, matching the connection port or larger than it); in any case, the possibility of providing another independent connection port in the bag holder (for connecting the bag to the delivery arrangement) is not excluded.

In an embodiment, when the bag holder is not mounted on the bottle holder, the injection system comprises a bottle connector arranged in the connection port; the bottle connector has a bottle connection element (for connecting to the bottle) and a delivery connection element in fluid communication with the bottle connection element (for connecting to the delivery arrangement). However, the bottle connector may be of any type, shape and size, and it may be arranged in the connection port in any way (for example, across a lateral port); moreover, the bottle connection element and the delivery connection element may be of any type (for example, a spike, septum, male/female luer fitting).

In an embodiment, when the bag holder is mounted on the bottle holder, the injection system comprises a bag connector arranged in the connection port; the bag connector has a bag connection element (for connecting to the bag) and a further delivery connection element in fluid communication with the bag connection element (for connecting to the delivery arrangement). However, the bag connector may be of any type, shape and size, and it may be arranged in the connection port in any way (either the same or different with respect to the bottle connector). Moreover, the bag connection element may be of any type (either the same or different with respect to the bottle connection element) and the further delivery connection element may be of any type (either exactly the same or simply compatible with the delivery connection element). In any case, the possibility of using a different delivery arrangement for the bag is not excluded.

In an embodiment, the bag holder comprises locking means that is switchable between a locking condition for locking the bag holder on the bottle holder and an unlocking condition for unlocking the bag holder from the bottle holder. However, the locking means may be implemented with any structure (for example, a latch) and at any position (for example, on the bottle holder), or it may even be omitted at all.

In an embodiment, a combination of the locking means with the first connector implements a ratchet mechanism for switching the locking means to the locking condition during the mounting of the bag holder on the bottle holder. However, the ratchet mechanism may be of any type (for example, with a friction arrangement for preventing any backlash); moreover, the locking means may be switched to the locking condition in any way during the mounting of the bag holder on the bottle holder (for example, with a dedicated mechanism independent of the corresponding connectors).

In an embodiment, the locking means comprises command means for switching the locking means to the unlocking condition in response to a manual command. However, the command means may be implemented with any structure (for example, a pull-button, a slider); in any case, the possibility of unlocking the bag holder from the bottle holder in another way (for example, by simply applying a sufficient force) is not excluded.

In an embodiment, a combination of the second connector with the first connector or the further first connector and a combination of the further second connector with the first connector implement a bayonet-type mount. In an embodiment, the bayonet-type mount is used for mounting the cover on the bottle holder or the bag holder and for mounting the bag holder on the bottle holder, respectively, with a first translation from a dismount condition to an interference condition followed by a first rotation from the interference condition to a mount condition; the bayonet-type mount is used for dismounting the cover from the bottle holder or the bag holder and for dismounting the bag holder from the bottle holder, respectively, with a second rotation opposite the first rotation from the mount condition to the interference condition followed by a second translation opposite the first translation from the interference condition to the dismount condition. However, the bayonet-type mount may be of any type (for example, with a cylindrical male component having radial pins and a female receptor with matching L-shaped slots); moreover, the (first and second) translations and rotations may have any direction and extent.

In an embodiment, the locking means comprises stopping means. However, the stopping means may be implemented in any way (for example, with a tooth pivoting around an end thereof).

In an embodiment, the locking means comprises resilient means for biasing the stopping means to the locking condition preventing the second rotation. However, the resilient means may be implemented with any structure (for example, directly by a flexible structure of the stopping means) and may bias the stopping means in any way (for example, with a pushing or pulling action) to cause it preventing the second rotation in any way (for example, by means of a tooth with a steep slope).

In an embodiment, the stopping means comprises leading means for interfering with the first connector during the first rotation to lead the stopping means to the unlocking condition allowing the first rotation in opposition to the resilient means. However, the leading means may be implemented with any structure (for example, a lever with a rounded profile).

In an embodiment, the command means comprises means for moving the stopping means to the unlocking position in opposition to the resilient means. However, the command means may move the stopping means in any way (for example, with a separate element acting on it).

In an embodiment, the bag holder comprises hooking means for hanging the bag. However, the hooking means may be implemented in any way (for example, with a lock for securing the bag on the hook).

In an embodiment, the bag holder comprises regulation means for regulating a position of the hooking means. However, the regulation means may be implemented in any way (for example, with a ratchet and a corresponding release system) and it may be used to regulate the position of the hooking means in any way (either in a continuous or discrete way, at any number of positions). In any case, the possibility of having the hooking means in a fixed position is not excluded.

In an embodiment, said at least one supply station further comprises a conditioning device for thermally conditioning the fluid to be injected in a chamber defined by the cover mounted on the bottle holder or on the bag holder. However, the chamber may be of any type, shape and size according to the cover (see above); moreover, the conditioning device may operate in any way (for example, to heat and/or to cool the fluid starting from any temperature, like the room temperature) and it may be of any type (for example, with any number of conditioning elements, down to a single one). In any case, the conditioning device may be provided in any number of supply stations (either the same or different with respect to the supply stations provided with the bag holder); conversely, a simplified implementation without any conditioning device is contemplated.

In an embodiment, the conditioning device crosses the opening when the bag holder is mounted on the bottle holder. However, the conditioning device may be arranged in any way (for example, mounted on the bottle holder or on the bag holder after its mounting on the bottle holder, embedded in the cover).

In an embodiment, said at least one supply station comprises means for mounting the conditioning device on the bottle holder. However, the conditioning device may be mounted on the holder in any way (for example, with a snap fitting).

In an embodiment, the first connector is provided on the conditioning device. However, the first connector may be provided at any position (for example, only on the bottle holder, on the conditioning device replacing the one on the bottle holder or in addition thereto).

In an embodiment, the conditioning device comprises a first conditioning element arranged around the connection port. However, the first conditioning element may be of any type, shape and size (for example, squared) and it may be arranged around the connection port in any way (for example, only partially surrounding it).

In an embodiment, the conditioning device comprises a second conditioning element extending transversally to the first conditioning element. However, the second conditioning element may be of any type, shape and size (for example, U-like) and it may extend transversally to the first conditioning element in any way (for example, obliquely, completely surrounding it). In any case, the conditioning device with these first and second conditioning elements leads itself to be used in (standard) injection systems as well (without the above-described bag holder).

In an embodiment, the first conditioning element extends horizontally in an operative condition of the injection system. However, the possibility of having the first conditioning element extending in another direction is not excluded (for example, vertically when the connection port is arranged laterally).

In an embodiment, the second conditioning element extends from a border of the first conditioning element. However, the second conditioning element may be arranged at any other position (either in contact with or spaced apart from the first conditioning element).

In an embodiment, the second conditioning element extends vertically in the operative condition of the injection system. However, the possibility of having the first conditioning element extending in another direction is not excluded (for example, horizontally when the connection port is arranged laterally).

In an embodiment, the first conditioning element completely surrounds the connection port in a plan view. However, the first condition element may surround the connection port in any way (for example, completely or only partially along its height).

In an embodiment, the first conditioning element comprises a ring that is formed by a disk having a through-hole matching the connection port. However, the ring may have any thickness and it may be formed by a disk having any size and with any through-hole matching the connection port in any way (for example, slightly narrower or larger than it).

In an embodiment, the second conditioning element partially surrounds the connection port. However, the second condition element may be arranged in any way around the connection port (for example, with multiple components distributed along its border).

In an embodiment, the second conditioning element extends along a circular arc. However, the second conditioning element may extend along any line (for example, with an elliptical shape).

In an embodiment, the circular arc subtends an angle of 220°-340°. However, the circular arc may have any other extent.

In an embodiment, the second conditioning element comprises a fin having a height decreasing from a center of the fin to each end thereof. However, the height of the fin may decrease in any way (for example, with one or more sections at constant height); more generally, the fin may have any other profile (even always with the same height).

In an embodiment, the first conditioning element comprises a first heating coil having a first resistance and the second conditioning element comprises a second heating coil having a second resistance higher than the first resistance. However, the heating coils may be of any type, shape and size; moreover, they may have any resistance, in either absolute or relative terms (with any one of them lower than, equal to or higher than the other one). More generally, any other implementation of the heating elements is contemplated (even not based on the Joule effect).

In an embodiment, the injection system comprises means for controlling the first conditioning element and the second conditioning element individually. However, the conditioning elements may be controlled either individually or always in the same way. Moreover, the control of the conditioning device may be implemented in any way. For example, the conditioning device may be controlled by any software program suitable to be used by any data processing or computing system or in connection therewith (for example, directly in the central unit) thereby configuring the system to perform the desired operations (for example, in the form of external or resident software, firmware, or microcode). The program may be provided on any computer readable storage medium or it may be downloaded to the corresponding computing system in any way (for example, via a network). In any case, the heating device may be controlled with a hardware structure (for example, a circuitry integrated in one or more chips) or with a combination of software and hardware suitably programmed or otherwise configured.

In an embodiment, the conditioning device comprises a plurality of temperature sensors each one for measuring a temperature in the chamber. However, the temperature sensors may be of any type, at any position and in any number (down to none).

In an embodiment, the injection system comprises means for detecting an error condition according to a comparison of the measured temperatures. However, the detection of the error condition may be implemented in any way (as above); moreover, the error condition may be detected according to any comparison of the measured temperatures (for example, according to a trend of their difference over time). In any case, this feature may also be omitted at all (for example, when a single temperature sensor is available).

In an embodiment, the conditioning device is a heating device for maintaining a target temperature in the chamber. However, the control of the temperature may be implemented in any way (as above); moreover, the target temperature may be maintained in any way within any range around any desired value (for example, by switching the heating device on when the measured temperature falls below the target temperature possibly minus a delta temperature and switching the heating device off when the measured temperature exceeds the target temperature possibly plus the delta temperature).

In an embodiment, the injection system is for injecting the fluids into the patient during a scan examination thereof; the fluids are one or more medical fluids comprising a contrast agent and/or a saline solution. However, the injection system may be used for any scan examination (for example, in MR, nuclear or ultrasound imaging applications); moreover, the injection system may be used with any contrast agent (for example, a barium-based contrast agent such as barium sulfate, gadolinium, a radioisotope, a suspension of gas-filled microbubbles), any saline solution (for example, with the addition of dextrose), any combination thereof or more generally with any medical fluid(s).

An embodiment provides a bag holder for use in the injection system described above; the bag holder comprises said further first connector and said further second connector. However, the bag holder may be put on the market as a stand-alone product to be used with pre-existing injection systems (with or without the above-described conditioning device), as a modification (after-market) kit for application thereto or directly integrated in (new) injection systems.

An embodiment provides an injection system for injecting one of more fluids into a patient; the injection system comprises one or more supply stations each one for supplying one of the fluids to be injected from a container. At least one of the supply stations comprises housing means defining a chamber for housing the container (the chamber having a connection port for connecting the container to a delivery arrangement for delivering the fluid to the patient) and a conditioning device for thermally conditioning the fluid in the chamber. The conditioning device comprises a first conditioning element arranged around the connection port and a second conditioning element extending transversally to the first conditioning element. However, the injection system (in this case, of syringe type as well) and the conditioning device may be of any type (see above).

An embodiment provides a conditioning device for use in the injection system described above; the conditioning device comprises said first conditioning element and said second conditioning element. However, the conditioning device may be put on the market as a stand-alone product to be used with pre-existing injection systems (with or without the above-described bag holder), as a modification (after-market) kit for application thereto or directly integrated in (new) injection systems.

Generally, similar considerations apply if the injection system, the bag holder and the conditioning device each has a different structure or comprises equivalent components (for example, of different materials), or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides method for operating an injection system for injecting one or more fluids into a patient. For at least one supply station comprised in the injection system (for supplying one of the fluids to be injected) the method comprises holding a bottle containing the fluid to be injected in a bottle holder, and mounting a cover on the bottle holder for covering the bottle by mating a first connector of the bottle holder with a second connector of the cover. The method further comprises mounting a bag holder on the bottle holder by mating the first connector of the bottle holder with a further second connector of the bag holder, holding a bag containing the fluid to be injected in the bag holder, and mounting the cover on the bag holder for covering the bag by mating a further first connector of the bag holder with the second connector of the cover. However, each supply station may be used only with the bottle holder, only with the bag holder or alternatively with both of them, and the different supply stations may be used in the same manner or in any combinations of different manners.

An embodiment provides a method for operating an injection system for injecting one or more fluids into a patient. For at least one supply station comprised in the injection system (for supplying one of the fluids to be injected from a container) the method comprises housing the container in a chamber (with the container connected to a delivery arrangement for delivering the fluid to the patient through a connection port of the chamber) and conditioning the medical fluid thermally in the chamber; said step of conditioning comprises conditioning the fluid thermally by a first conditioning element arranged around the connection port and by a second conditioning element extending transversally to the first conditioning element.

The above-described steps only relate to a control method of the injection system, which is completely independent of the actual injection of the fluids into the patient; in any case, the injection may also be performed in a non-invasive manner without any substantial physical intervention on the patient that would require professional medical expertise or entail any health risk for the patient (for example, intramuscularly). Therefore, this method is merely directed to the operation of the injection system without itself providing any functional interaction with the effects produced by the injection system on the patient Generally, similar considerations apply if the same solution is implemented with an equivalent method by using similar steps with the same functions of more steps or portions thereof, removing some steps being non-essential, or adding further optional steps); moreover, the steps may be performed in a different order, concurrently or in an interleaved way (at least in part).

The invention claimed is:

1. An injection system (200;700) for injecting one or more fluids into a patient, the injection system (200;700) comprising one or more supply stations (105a;105b) for supplying one of the one or more fluids to be injected, wherein at least one of the one or more supply stations (105a;105b) comprises:
   a bottle holder (115a;115b) for holding a bottle (110a;110b) containing the one or more fluids to be injected, the bottle holder (115a;115b) comprising a first connector (415;1135), and
   a cover (120a;120b) for covering the bottle (110a;110b) when held on the bottle holder (115a;115b), the cover (120a;120b) comprising a second connector (420) for mating with the first connector (415;1135) to mount the cover (120a;120b) on the bottle holder (115a;115b), characterized in that
said at least one of said one or more supply stations (105a;105b) further comprises:
   a bag holder (205a;205b) for holding a bag (605) containing the one or more fluids to be injected, the bag holder (205a;205b) comprising a further second connector (425) for mating with the first connector (415;1135) to mount the bag holder (205a;205b) on the bottle holder (115a;115b) and a further first connector (430) for mating with the second connector (420) to mount the cover (120a;120b) on the bag holder (205a;205b).

2. The injection system (200;700) according to claim 1, wherein the injection system (200;700) comprises a delivery arrangement (135,145) for delivering the one or more fluids to the patient, the bottle holder (115a;115b) comprising a connection port (132a;132b) for connecting the bottle (110a;110b) to the delivery arrangement (135,145) and the bag holder (205a;205b) comprising an opening (307) for accessing the connection port (132a;132b) to connect the bag (605) to the delivery arrangement (135,145) in the connection port (132a;132b) across the opening (307).

3. The injection system (200;700) according to claim 2, wherein when the bag holder (205a;205b) is not mounted on the bottle holder (115a;115b) the injection system (200;700) comprises, a bottle connector (130a;130b) arranged in the connection port (132a;132b) having a bottle connection element for connecting to the bottle (110a;110b) and a delivery connection element in fluid communication with the bottle connection element for connecting to the delivery arrangement (135,145), and wherein when the bag holder (205a;205b) is mounted on the bottle holder (115a;115b) the injection system (200;700) comprises a bag connector (630) arranged in the connection port (132a;132b) having a bag connection element (635) for connecting to the bag (605) and a further delivery connection element (640) in fluid communication with the bag connection element (635) fore connecting to the delivery arrangement (135,145).

4. The injection system (700) according to claim 2, wherein said at least one of said one or more supply stations (150a;105b) further comprises a conditioning device (705a;705b) for thermally conditioning the one or more fluids to be injected in a chamber defined by the cover (120a;120b) mounted on the bottle holder (115a,115b) or on the bag holder (205a;205b).

5. The injection system (700) according to claim 4, wherein the conditioning device (705a;705b) crosses the opening (307) when the bag holder (205a;205b) is mounted on the bottle holder (115a;115b).

6. The injection system (700) according to claim 4, wherein said at least one of said one or more supply stations (105a;105b) comprises means (1122,1125) for mounting the conditioning device (705a;705b) on the bottle holder (115;115b), the first connector (1135) being provided on the conditioning device (705a;705b).

7. The injection system (700) according to claim 4, wherein the conditioning device (705a;705b) comprises a first conditioning element (710a,710b) arranged around the opening (307) and a second conditioning element (715a;715b) extending transversally to the first conditioning element (710a;710b).

8. The injection system (200;700) according to claim 1, wherein the bag holder (205a;205b) comprises locking means (505) switchable between a locking condition for locking the bag holder (205a;205b) on the bottle bolder (115a;115b) and an unlocking, condition for unlocking the bag holder (205a;205b) from the bottle holder (115a;115b).

9. The injection system (200;700) according to claim 8, wherein a combination of the locking means (505) with the first connector (415;1135) implements a ratchet mechanism for switching the locking means (505) to the locking condition during the mounting of the bag holder (205a;205b) on the bottle holder (115a;115b), the locking means (505) comprising command means (535) for switching the locking means (505) to the unlocking condition in response to a manual command.

10. The injection system (200;700) according to claim 9, wherein a combination of the second connector (420) with the first connector (415;1135) or the further first connector (430) and a combination of the further second connector (425) with the first connector (415;1135) implement a bayonet-type mount for mounting the cover (120a;120b) on the bottle holder (115a;115b) or the bag holder (205a;205b) and for mounting the bag holder (205a;205b) on the bottle holder (115a;115b), respectively, with a first translation from a dismount condition to an interference condition followed by a first rotation from the interference condition to a mount condition and for dismounting the cover (120a;120b) from the bottle holder (115a;115b) or the bag holder (205a;205b) and for dismounting the bag holder (205a;205b) from the bottle holder (115a;115b), respectively, with a second rotation opposite the first rotation from the mount condition to the interference condition followed by a second translation opposite the first translation from the interference condition to the dismount condition.

11. The injection system (200;700) according to claim 10, wherein the locking means (505) comprises a stopping means (510) and a resilient means (540), the resilient means (540) for biasing the stopping means (510) to the locking condition preventing the second rotation, the stopping means (510) comprising leading means (530) for interfering with the first connector (415;1135) during the first rotation to lead the stopping means (510) to the unlocking condition allowing the first rotation in opposition to the resilient means (540), the command means (535) comprising means (535) for moving the stopping means (510) to the unlocking position in opposition to the resilient means (540).

12. The injection system (200;700) according to claim 1, wherein the bag holder (205a;205b) comprises hooking means (325) for hanging the bag (605) and regulation means (320,560-570) for regulating a position of the hooking means (325).

13. The injection system (200;700) according to claim 1, wherein the injection system (200;700) is for injecting the one or more fluids into the patient during a scan examination of the patient, the one or more fluids being one or more medical fluids comprising a contrast agent and/or a saline solution.

14. The injection system (200;700) according to claim 1, wherein a combination of the second connector (420) with the first connector (415;1135) or the further first connector (430) and a combination of the further second connector (425) with the first connector (415;1135) implement a bayonet-type mount for mounting the cover (120a;120b) on the bottle holder (115a;115b) or the bag holder (205a;205b) and for mounting the bag holder (205a;205b) on the bottle bolder (115a;115b), respectively, with a first translation from a dismount condition to an interference condition followed by a first rotation from the interference condition to a mount condition and for dismounting the cover (120a;120b) from the bottle holder (115a;115b) or the bag holder (205a;205b) and for dismounting the bag holder (205a;205b) from the bottle holder (115a;115b), respectively, with a second rotation opposite the first rotation from the mount condition to the interference condition followed by a second translation opposite the first translation from the interference condition to the dismount condition.

15. The injection system (700) according to claim 1, wherein said at least one of said one or more supply stations (150a;105b) further comprises a conditioning device (705a; 705b) for thermally, conditioning the one or more fluids to be injected in a chamber defined by the cover (120a;120b) mounted on the bottle holder (115a,115b) or on the bag holder (205a;205b).

16. A method for operating an injection system (200;700) for injecting one or more fluids into a patient, wherein for at least one supply station (105a;105b) comprised in the injection system (200) for supplying one of the one or more fluids to be injected the method comprises:

holding a bottle (110a;110b) containing the one or more fluids to be injected in a bottle holder (115a;115b), mounting a cover (120a;120b) on the bottle holder (115a; 115b) for covering the bottle (110a;110b) by mating a first connector (415;1135) of the bottle holder (115a; 115b) with a second connector (420) of the cover (120a;120b), characterized by mounting a bag holder (205a;205b) on the bottle holder (115a;115b) by mating the first connector (415;1135) of the bottle holder (115a;115b) with a further second connector (425) of the bag holder (205a;205b), holding a bag (605) containing the one or more fluids to be injected in the bag holder (205a;205b), and mounting the cover (120a;120b) on the bag holder (205a; 205b) for covering the bag (650) by mating a further first connector (430) of the bag holder (205a;205b) with the second connector (420) of the cover (120a; 120b).

\* \* \* \* \*

UNITED STATES PATENT AND TRADEMARK OFFICE
CERTIFICATE OF CORRECTION

PATENT NO.        : 10,398,829 B2
APPLICATION NO.   : 16/067421
DATED             : September 3, 2019
INVENTOR(S)       : Pierre Yves Chassot et al.

Page 1 of 1

It is certified that error appears in the above-identified patent and that said Letters Patent is hereby corrected as shown below:

In the Claims

Column 23, Line 62, Claim 3, the phrase "comprises, a bottle" should read –comprises a bottle–.

Column 24, Line 6, Claim 3, the word "fore" should read –for–.

Column 24, Line 27, Claim 7, the phrase "710a,710b" should read –710a;710b–.

Column 24, Line 34, Claim 8, the word "bolder" should read –holder–.

Column 24, Line 35, Claim 8, the phrase "unlocking, condition" should read –unlocking condition–.

Column 25, Line 29, Claim 14, the word "bolder" should read –holder–.

Column 26, Line 7, Claim 15, the phrase "thermally, conditioning" should read –thermally conditioning–.

Signed and Sealed this
Twelfth Day of November, 2019

Andrei Iancu
*Director of the United States Patent and Trademark Office*